United States Patent
Angel et al.

(10) Patent No.: US 9,421,080 B2
(45) Date of Patent: Aug. 23, 2016

(54) MULTI-LUMEN CENTRAL ACCESS VENA CAVA FILTER APPARATUS FOR CLOT MANAGEMENT AND METHOD OF USING SAME

(71) Applicant: BiO2 Medical, Inc., San Antonio, TX (US)

(72) Inventors: Luis F. Angel, San Antonio, TX (US); Elijah Wade Atkinson, Westminster, CO (US); Rogelio Ivan Guerra, Lakewood, CO (US); Jeffrey N. Steinmetz, Arvada, CO (US); Jeremy Morgan, Idaho Spring, CO (US)

(73) Assignee: BIO2 MEDICAL, INC., Golden, CO (US)

( * ) Notice: Subject to any disclaimer, the term of this patent is extended or adjusted under 35 U.S.C. 154(b) by 446 days.

(21) Appl. No.: 13/918,841

(22) Filed: Jun. 14, 2013

(65) Prior Publication Data
US 2013/0345627 A1    Dec. 26, 2013

Related U.S. Application Data

(63) Continuation of application No. 13/874,227, filed on Apr. 30, 2013.

(60) Provisional application No. 61/640,469, filed on Apr. 30, 2012.

(51) Int. Cl.
*A61F 2/01* (2006.01)
*A61B 17/22* (2006.01)
(Continued)

(52) U.S. Cl.
CPC ............... *A61F 2/01* (2013.01); *A61B 17/221* (2013.01); *A61B 17/22031* (2013.01); *A61M 25/003* (2013.01); *A61B 2017/00349* (2013.01); *A61B 2017/22042* (2013.01); *A61B 2090/081* (2016.02); *A61F 2/013* (2013.01);
(Continued)

(58) Field of Classification Search
CPC .... A61F 2/01; A61F 2/013; A61F 2002/016; A61F 2002/018; A61B 2017/00022; A61B 2017/320004; A61B 2017/22042; A61B 2017/00349; A61B 17/320783; A61B 17/320725; A61B 17/320758; A61B 17/22031; A61B 17/221; A61B 2019/4852; A61B 2019/4836; A61M 31/005; A61M 31/003; A61M 2025/0003
See application file for complete search history.

(56) References Cited

U.S. PATENT DOCUMENTS 5,353,804 A * 10/1994 Kornberg ............ A61B 10/0266
                                                600/567
5,833,605 A * 11/1998 Shah ........................ G01B 7/13
                                                33/512

(Continued)

OTHER PUBLICATIONS

European Search Report issued in corresponding foreign application, pp. 1-6 (Sep. 11, 2015).

(Continued)

*Primary Examiner* — Jocelin Tanner
(74) *Attorney, Agent, or Firm* — David G. Rosenbaum; Benjamin D. Rotman; Rosenbaum IP, P.C.

(57) ABSTRACT

A combined multi-lumen central access catheter and an embolic filter including ports proximal and distal the filter for fluid infusion and/or pressure sensing and infusion ports in the catheter to permit infusion of bioactive agents, flushing agents and/or contrast agents and managing the capture of the clot thereafter.

8 Claims, 28 Drawing Sheets

(51) Int. Cl.
*A61M 25/00* (2006.01)
*A61B 17/221* (2006.01)
*A61M 31/00* (2006.01)
*A61B 17/00* (2006.01)

(52) U.S. Cl.
CPC ....... *A61F2002/018* (2013.01); *A61M 31/005* (2013.01); *A61M 2025/0003* (2013.01)

(56) References Cited

U.S. PATENT DOCUMENTS

| | | | | |
|---|---|---|---|---|
| 6,405,733 | B1* | 6/2002 | Fogarty | A61B 19/54 128/899 |
| 6,558,401 | B1 | 5/2003 | Azizi | 606/159 |
| 9,125,728 | B2* | 9/2015 | Angel | A61F 2/01 |
| 2002/0016564 | A1 | 2/2002 | Courtney et al. | 604/96.01 |
| 2003/0130681 | A1* | 7/2003 | Ungs | A61F 2/013 606/200 |
| 2003/0191493 | A1* | 10/2003 | Epstein | A61B 17/22 606/200 |
| 2004/0102806 | A1 | 5/2004 | Broome et al. | 606/200 |
| 2005/0228417 | A1 | 10/2005 | Teitelbaum et al. | 606/159 |
| 2006/0178695 | A1* | 8/2006 | Decant | A61B 5/02007 606/200 |
| 2007/0167804 | A1* | 7/2007 | Park | A61B 5/0066 600/459 |
| 2009/0062840 | A1 | 3/2009 | Angel | 606/200 |
| 2009/0264915 | A1 | 10/2009 | WasDyke | 606/200 |
| 2010/0217304 | A1* | 8/2010 | Angel | A61F 2/013 606/200 |
| 2011/0208134 | A1 | 8/2011 | Castella et al. | 604/266 |
| 2012/0022579 | A1 | 1/2012 | Fulton | 606/200 |
| 2012/0059356 | A1 | 3/2012 | di Palma et al. | 604/509 |
| 2013/0190803 | A1 | 7/2013 | Angel et al. | 606/200 |
| 2013/0204206 | A1 | 8/2013 | Morgan et al. | 604/246 |
| 2013/0317425 | A1* | 11/2013 | Angel | A61F 2/01 604/93.01 |

OTHER PUBLICATIONS

Decousus, H., et al., "A clinical trial of vena caval filters in the prevention of pulmonary embolism in patients with proximal deep-vein thrombosis" *The New England Journal of Medicine* 338(7): 409-415 (1998).

International Search Report issued in corresponding foreign application, PCT/US2013/038918, pp. 1-6 (Aug. 14, 2013).

Lin, P., et al., "Vena caval filters in the treatment of acute DVT" *Endovascular Today* pp. 40-50 (Jan. 2005).

Written Opinion issued in corresponding foreign application, PCT/US2013/038918, pp. 1-4 (Aug. 14, 2013).

International Preliminary Report on Patentability issued in corresponding foreign application, pp. 1-9 (Nov. 13, 2014).

* cited by examiner

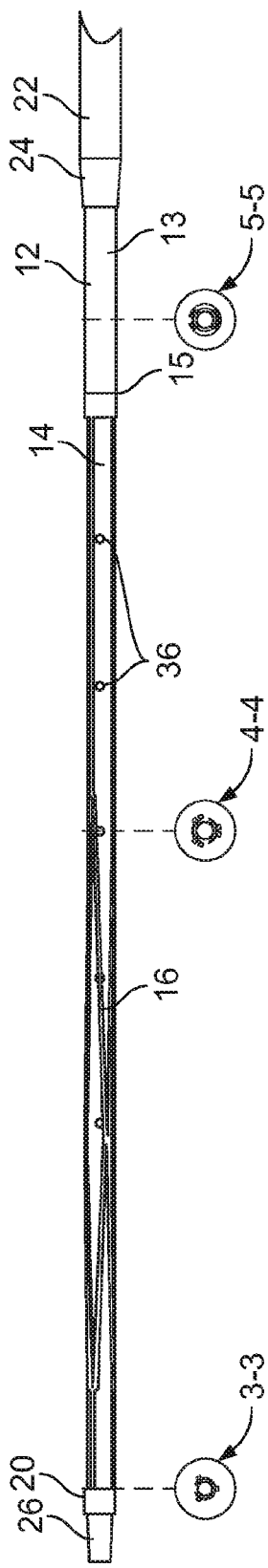
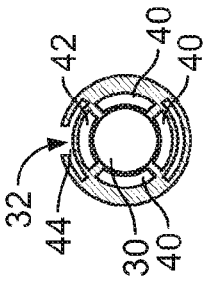
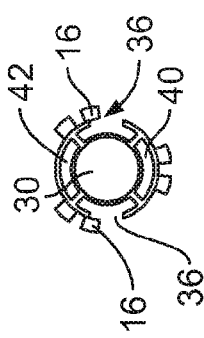
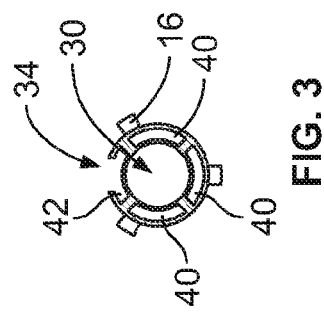

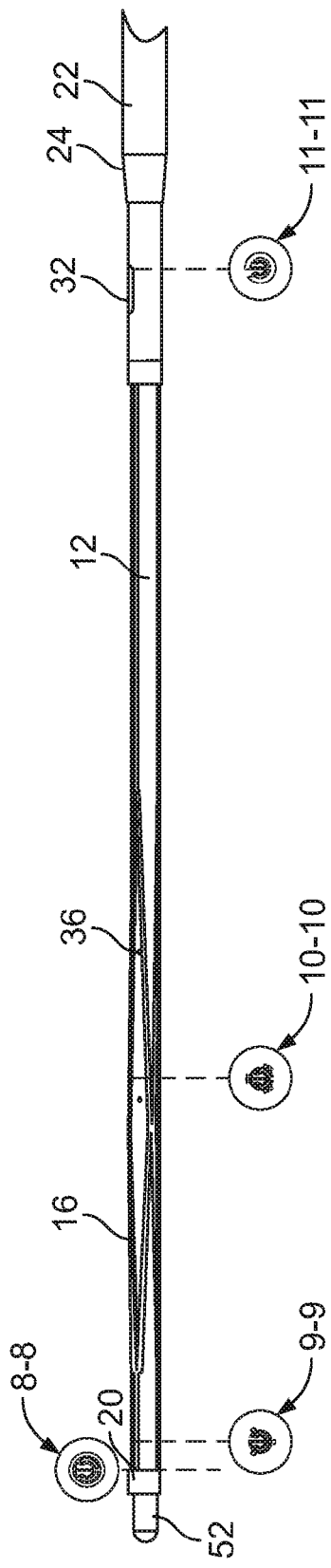
FIG. 7
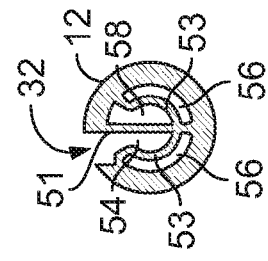
FIG. 11
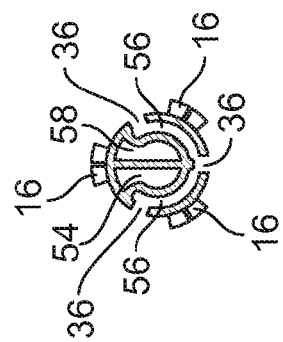
FIG. 10
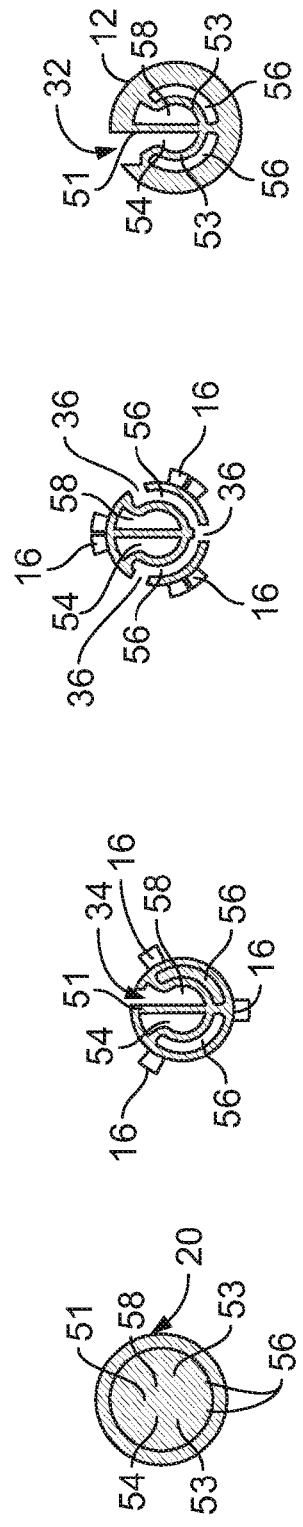
FIG. 9
FIG. 8

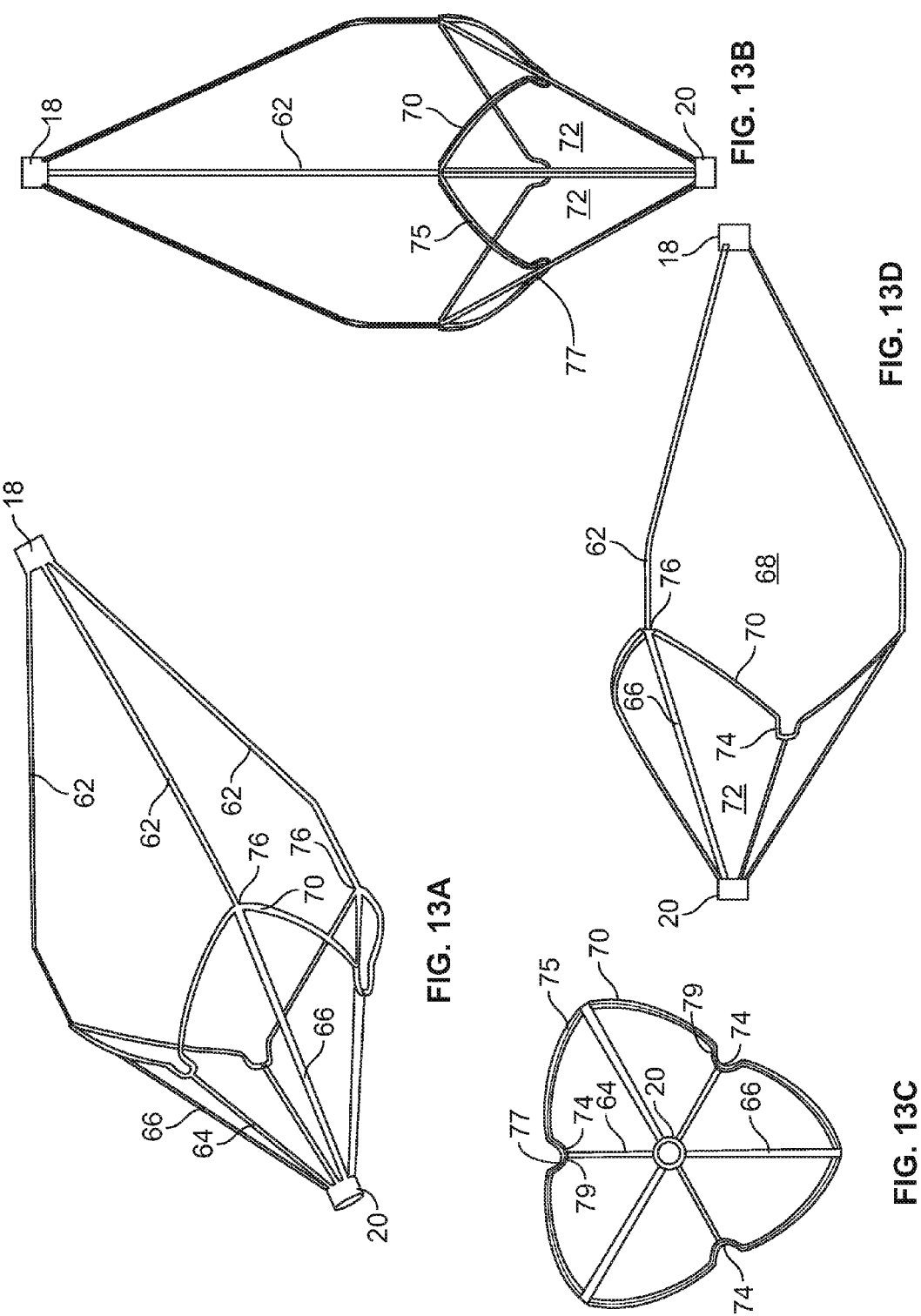

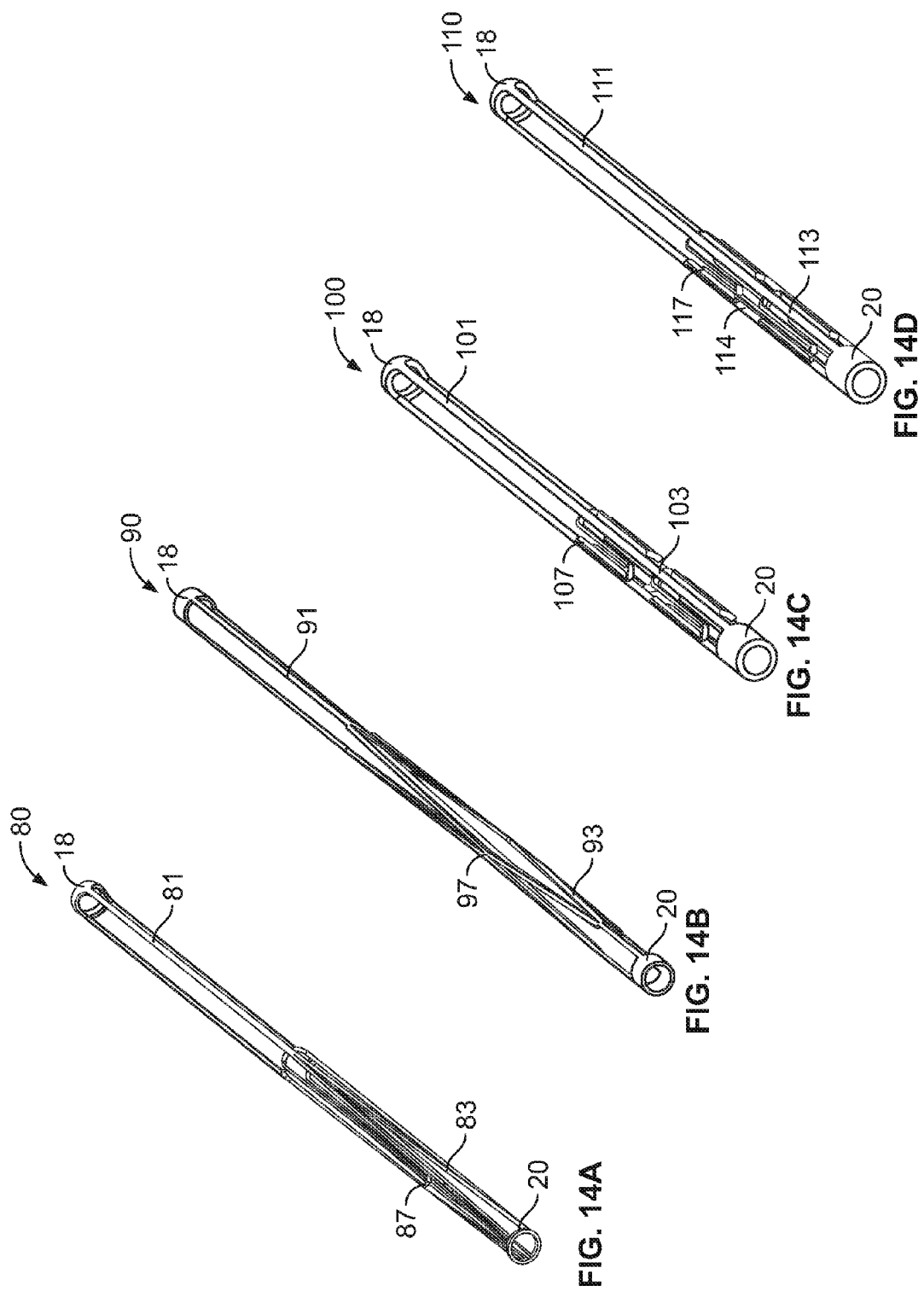

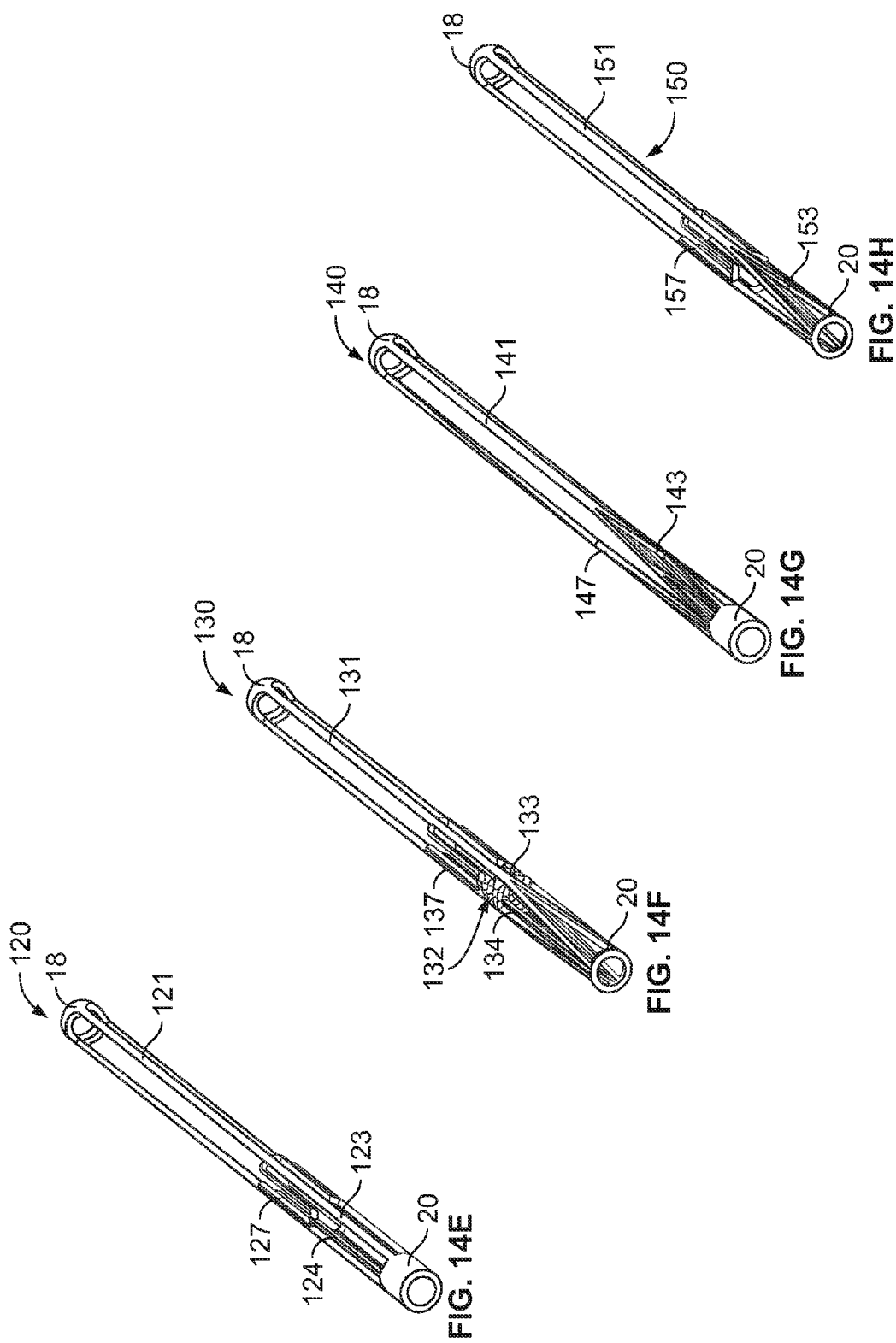

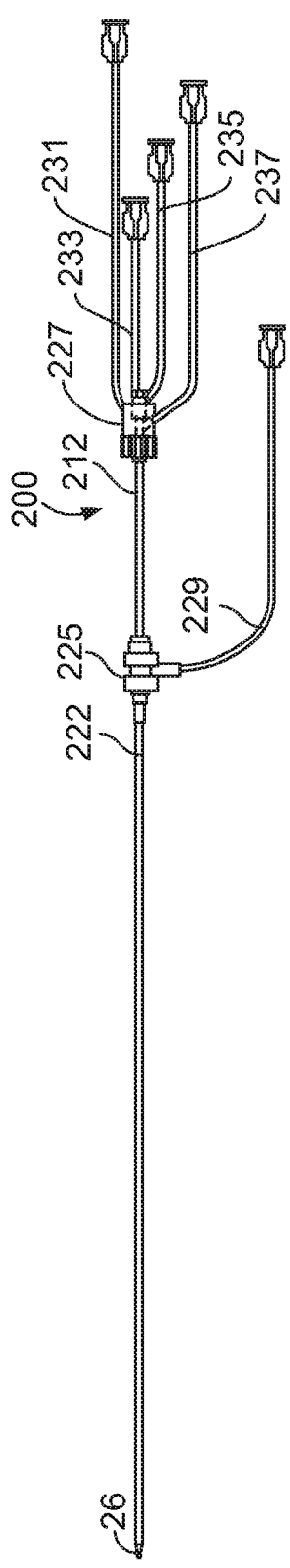
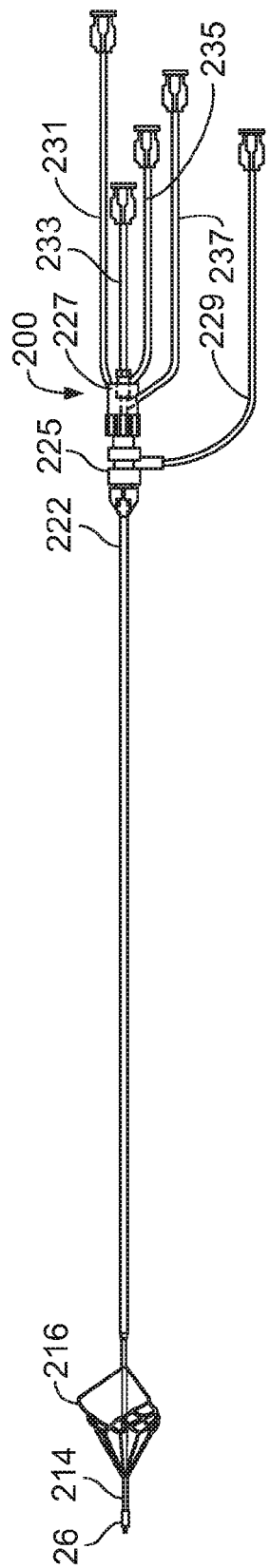
FIG. 16A
FIG. 16B

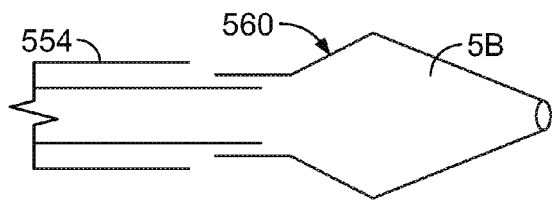
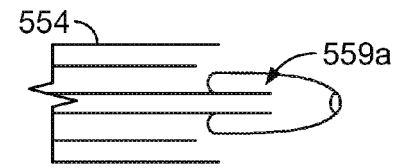
FIG. 24C    FIG. 24D
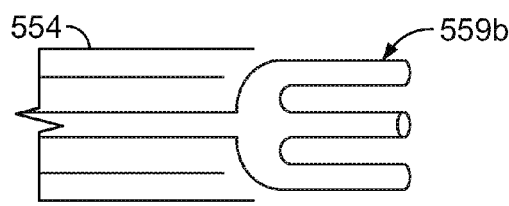
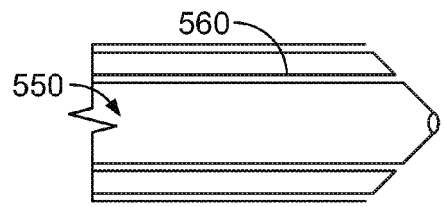
FIG. 24E    FIG. 24F
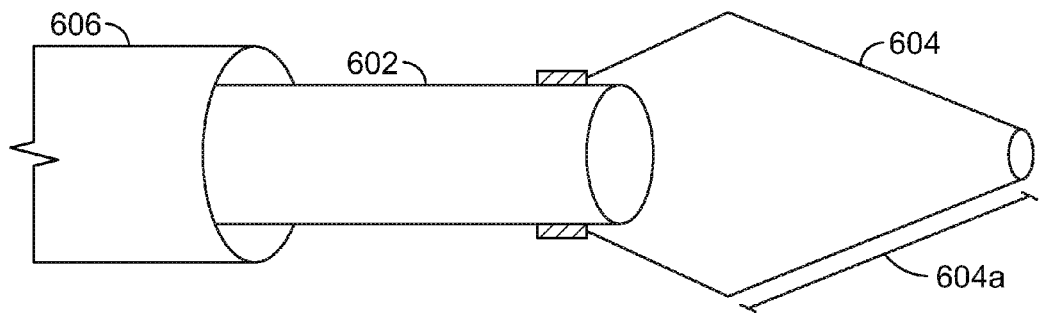
FIG. 25A

MULTI-LUMEN CENTRAL ACCESS VENA CAVA FILTER APPARATUS FOR CLOT MANAGEMENT AND METHOD OF USING SAME

CROSS-REFERENCE TO RELATED APPLICATIONS

This application is a continuation of U.S. patent application Ser. No. 13/874,227, filed Apr. 30, 2013, which claims priority to U.S. Patent Provisional Application Ser. No. 61/640,469 filed Apr. 30, 2012, which is herein incorporated by reference in its entirety.

BACKGROUND OF THE INVENTION

The present invention pertains generally to the field of vascular filters for capturing embolic material in the blood flow.

The accepted standard of care for patients with venous thromboembolism (VTE) is anticoagulant therapy. Inferior vena cava (IVC) filters are reserved for those patients who fail anticoagulant therapy, or have a complication or contraindication to anticoagulant therapy. Until the early 1970's, the only method of IVC interruption was surgical, either by clipping, ligation or plication. The first clinical experience of an endoluminally-placed device to interrupt IVC flow was reported by Mobin-Uddin et al. in 1969. However, it was not until the introduction of a stainless steel umbrella-type filter by Greenfield et al. in 1973 that an effective method of endoluminally trapping emboli while simultaneously preserving IVC flow became possible. Indeed, for many years, the Greenfield filter set a benchmark by which newer filters were measured. Early generations of filters were inserted by surgical cut-down and venotomy. Eventually filters were able to be inserted percutaneously: initially through large 24 Fr sheaths, though newer generations of filters are able to be delivered through 6 Fr systems.

Despite the safety and efficacy of modern day filters, systemic anticoagulation remains the primary treatment for VTE. Either unfractionated or low molecular weight heparin followed by three months of oral anticoagulation in patients with proximal deep venous thrombosis (DVT) is approximately 94% effective in preventing pulmonary embolism (PE) or recurrent DVT. The routine placement of IVC filters in addition to anticoagulation in patients with documented DVT was investigated by Decousus et al. in a randomized trial. Decousus H, Leizorovicz A, Parent F, et al. *A clinical trial of vena caval filters in the prevention of pulmonary embolism in patients with proximal deep-vein thrombosis. N Engl J Med* 1998; 338:409-415. This study revealed that the use of a permanent filter in addition to heparin therapy significantly decreased the occurrence of PE within the first 12 days compared to those without a filter. However, no effect was observed on either immediate or long-term mortality, and by 2 years, the initial benefit seen in the group of patients with filters was offset by a significant increase in the rate of recurrent DVT.

Despite the efficacy of anticoagulant therapy in the management of VTE, there are certain situations and conditions in which the benefits of anticoagulation are outweighed by the risks of instituting such a therapy. These include contraindications and complications of anticoagulant therapy. In such circumstances, there may be absolute or relative indications for filter insertion Currently, there are eight different types of permanent cava filters that are FDA approved. These include the Bird's Nest filter (Cook Incorporated, Bloomington, Ind.), Vena Tech LGM filter (B. Braun, Bethlehem Pa.), Vena Tech LP (B. Braun), Simon Nitinol filter (Bard, Covington, Ga.), Titanium Greenfield filter (Boston Scientific, Natick Mass.), Over-the-Wire Greenfield filter (Boston Scientific), TrapEase filter (Cordis Corp.) and the Günther Tulip filter (Cook Inc.)

Well-founded concerns over the long-term complications of permanent IVC filters, particularly in younger patients in need of PE prophylaxis with a temporary contraindication to anticoagulation, has led to the development of temporary and retrievable filters. Temporary filters remain attached to an accessible transcutaneous catheter or wire. These have been used primarily in Europe for PE prophylaxis during thrombolytic therapy for DVT. Currently these devices are not approved for use in the United States. Retrievable filters are very similar in appearance to permanent filters, but with modifications to the caval attachment sites and/or hooks at one end that can facilitate their removal. Retrievable filters are currently available in the United States, examples of these include the Günther Tulip (Cook Inc.), Opt Ease (Cordis Corp.), and Recovery nitinol filters (Bard Peripheral Vascular, Tempe, Ariz.) Lin P H, et al., *Vena caval filters in the treatment of acute DVT. Endovascular Today* 2005; January:40-50. The time limit of retrievability is in part dependant on the rate of endothelialization of the device, which typically occurs within 2 weeks. However, differences in design may extend the time period in which the filter may be safely retrieved.

Currently no consensus exists as to which patients have an indication for a retrievable filter. However, it is generally accepted that patients at high risk for pulmonary embolism or with documented PE and with a temporary contraindication to anticoagulation are candidates.

Certain circumstances preclude the placement of a filter in the infrarenal IVC. This includes thrombus extending into the infrarenal IVC, renal vein thrombosis or pregnancy. The safety of suprarenal placement of IVC filters is well documented, with no reported instances of renal dysfunction and no differences in the rates of filter migration, recurrent PE or caval thrombosis.

The rate of upper extremity DVT is on the rise. This is predominantly due to an increasing number of patients having short- and long-term upper extremity central venous access catheters. In one study, 88% of patients found to have an upper extremity DVT had a central venous catheter present at the site of thrombosis at the time of diagnosis or within the previous two weeks. Pulmonary embolism may complicate upper extremity DVT in 12-16% of cases. In patients who have such a complication or contraindication to anticoagulation, a filter can be safely placed immediately below the confluence of the brachiocephalic veins. However, misplacement of an SVC filter is theoretically more likely than with an IVC filter because of the relatively short target area for deployment.

The most common imaging modality used for filter insertion is fluoroscopy, performed either in an interventional suite or an operating room. Bedside placement of filters has inherent advantages, particularly for critically ill patients in intensive care settings where transport can be avoided. Portable fluoroscopy, surface duplex ultrasound and intravascular ultrasound (IVUS) have all been used to assist with bedside filter placement.

Vena cava filter placement frequently occurs concomitantly with central access line placement or in critically ill patients that already have a central access line in place.

Heretofore, however, there have been no devices which combine the function of a central access catheter and a removable vena cava filter.

SUMMARY OF THE INVENTION

A multi-lumen catheter coupled to a vena cava filter that is useful both as a central venous access catheter for administration of intravenous fluids, bioactive agents, contrast agents, flushing agents, pressurized fluids for thrombolysis and/or withdrawal of blood samples and for capture of thrombus or emboli and managing the capture of the clot thereafter.

BRIEF DESCRIPTION OF THE DRAWINGS

FIG. 2 is a side elevational view of a central venous access vena cava filter catheter in accordance with the first embodiment of the present invention.

FIG. 3. is a cross-sectional view taken along line 3-3 of FIG. 2.

FIG. 4 is a cross-sectional view taken along line 4-4 of FIG. 2.

FIG. 5 is a cross-sectional view taken along line 5-5 of FIG. 2.

FIG. 7 is a side elevational view of a central venous access vena cava filter catheter in accordance with the second embodiment of the present invention.

FIG. 8 is a cross-sectional view taken along line 8-8 of FIG. 7.

FIG. 9 is a cross-sectional view taken along line 9-9 of FIG. 7.

FIG. 10 is a cross-sectional view taken along line 10-10 of FIG. 7.

FIG. 11 is a cross-sectional view taken along line 11-11 of FIG. 7.

FIG. 13A is a perspective view of a vena cava filter member in accordance with a first embodiment thereof.

FIG. 13B is a first side elevational view thereof.

FIG. 13C is an end elevational view thereof.

FIG. 13D is a second side elevational view thereof.

FIGS. 14A-14H are perspective views of alternative embodiments of a vena cava filter member in accordance with the present invention.

FIG. 16A is a side elevational view of the vena cava central line catheter in its undeployed state.

FIG. 16B is a side elevational view of the vena cava central line catheter in its deployed state.

FIGS. 24A-24F are cross-sectional views of the multi-step options for deploying a temporary dilator for clot management.

FIGS. 25A-25C are cross-sectional views of a thrombus present during retraction of the filter while the outer sheath stretches over the filter and constricts the clot into the single lumen inner shaft and/or the inner area of the filter.

DETAILED DESCRIPTION OF THE PREFERRED EMBODIMENTS

Figure 1:
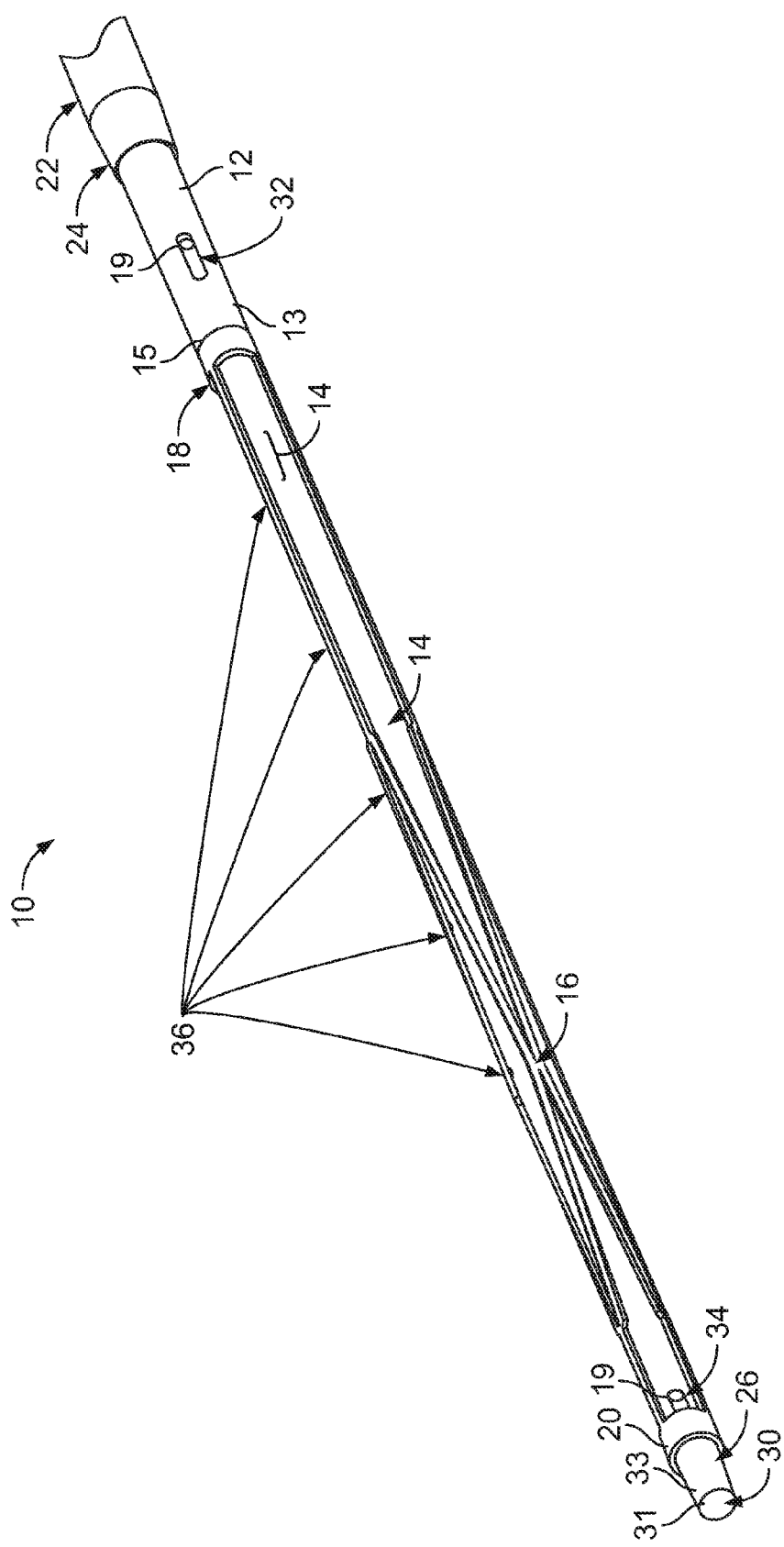
FIG. 1 is a perspective view of a central venous access vena cava filter catheter in accordance with a first embodiment of the present invention with the vena cava filter in an unexpanded state.
Figure 6:
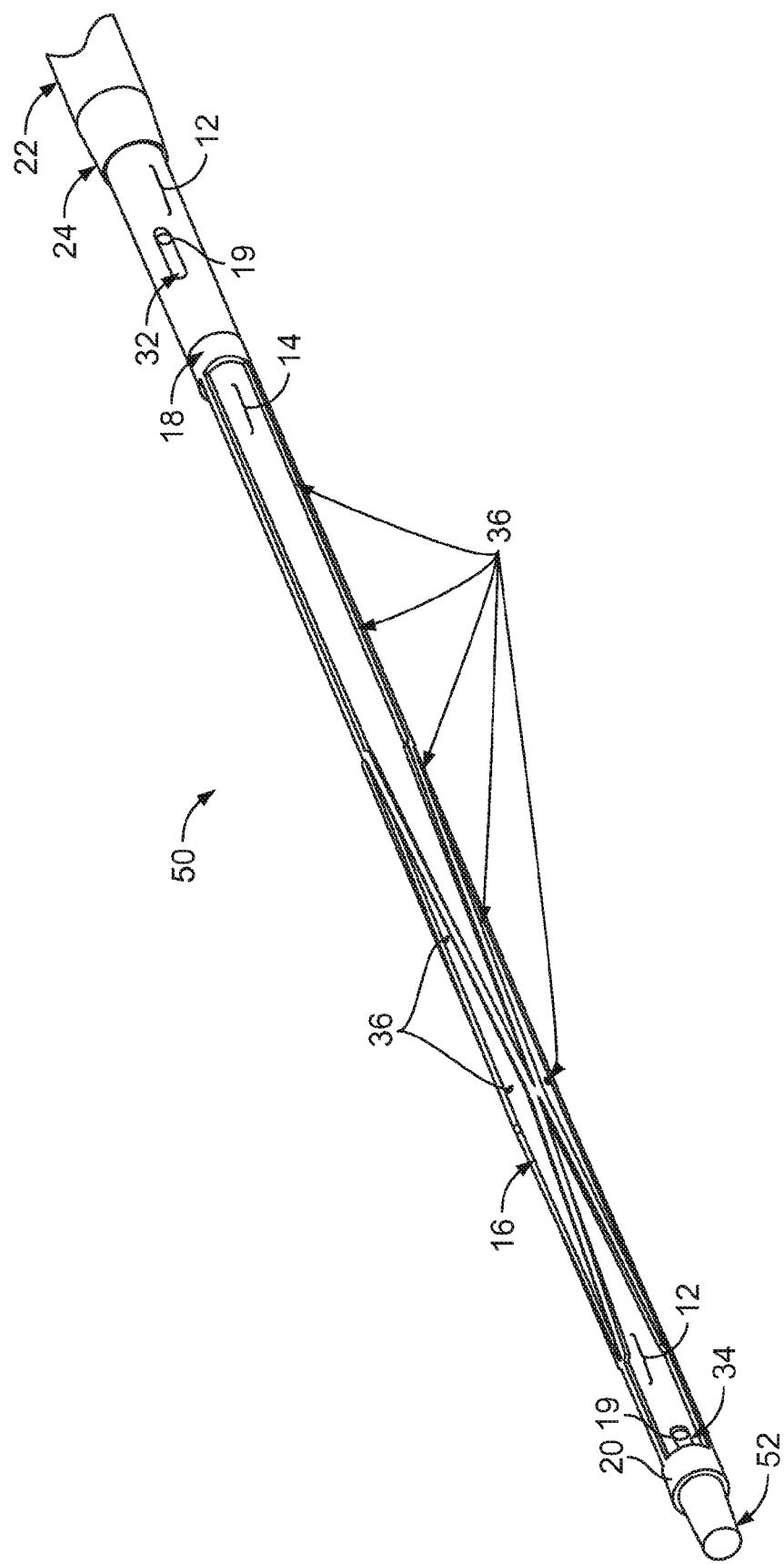
FIG. 6 is a perspective view of a central venous access vena cava filter catheter in accordance with a second embodiment of the present invention illustrating the vena cava filter in an unexpanded state.

Accordingly, it is an objective of the present invention to provide a multi-lumen catheter coupled to a vena cava filter that is useful both as a central venous access catheter for administration of intravenous fluids, bioactive agents, contrast agents, flushing agents, pressurized fluids for mechanical thrombolysis and/or withdrawal of blood samples and for capture of thrombus or emboli and managing a clot burdened filter in the expanded and contracted state of the filter.

The present invention may be configured for either a femoral approach or a jugular approach to the inferior vena cava. Vena cava filters are typically deployed infrarenaly, but may also be deployed suprarenaly. It will be understood that within the inferior vena cava blood flow is superior, i.e., toward the patients head. Thus, in all embodiments, the vena cava filter will be positioned so that it opens inferiorly, i.e., away from the patient's head and toward the direction of the blood flow. It will be appreciated, therefore, that in the present invention, the vena cava filter will have a different axial orientation on the central access catheter depending upon whether the device is intended for use in a femoral approach or a jugular approach.

Another aspect of the present invention is to provide a filter geometry in which the proximal portion of the filter, relative to the axis of blood flow, has larger interstitial openings to permit thrombus or embolic material to flow into the filter, while the distal portion of the filter, again relative to the axis of blood flow, has relatively smaller interstitial openings that capture the thrombus or embolic material within the filter. Another way to view this aspect is that the structure of the filter includes a greater open surface area exposed to the flow of embolic material into the filter at its proximal end, while the distal end has smaller open surface area exposed to the flow of embolic material to capture the embolic material in the distal end of the filter member. More specifically, regardless of whether the present invention is delivered by a jugular approach or a femoral approach, the filter geometry is such that the larger interstitial openings of the filter are positioned inferiorly along a longitudinal axis of the filter.

In the accompanying Figures like structural or functional elements are designated by like reference numerals, e.g., 16, 116, 216, 316, 416 represent similar structural or functional elements across different embodiments of the invention. With particular reference to FIGS. 1-5, according to a first embodiment of the invention, there is disclosed a central venous access filter ("CVAF") 10 that is composed generally of a multi-lumen central venous access catheter body 12 having a proximal port 32 associated with a first lumen 44 and a distal port 34 associated with a second lumen 42, a filter member 16, having a first end 18 and a second end 20, is positioned generally intermediate the distal port 34 and the proximal port 32 and is generally concentric relative to the catheter body 12. An outer sheath 22 is concentrically disposed over the catheter body 12 such that relative movement of the catheter body 12 and the outer sheath 22 either exposes the filter member 16 or captures the filter member 16 within the outer sheath 22. The outer sheath 22 terminates in an annular opening at a distal end thereof and at first hub member 225 as depicted in FIGS. 16A and 16B. The proximal hub 225 will be described more fully hereinafter. The proximal hub may be employed as described in commonly assigned U.S. patent application Ser. No. 13/737,694, herein incorporated by reference in its entirety. The catheter body 12 extends through a central bore in the proximal hub 225 and passes through a central lumen of the outer sheath 22. A second hub member 227, as depicted in FIGS. 16A and 16B, is coupled to a proximal end of the catheter body 12. The second hub member 227 and the first hub member 225 are removably engageable with each other as will also be described further hereinafter.

Depending upon the orientation of the filter member 16, the first end 18 or the second end 20 may either be fixed or moveable relative to the catheter body 12. Alternatively, as will be discussed further hereinafter, the filter member 16 may have only a first end 18 which is fixed to the catheter body 12

To facilitate percutaneous introduction of the inventive CVAF 10, a physician may optionally elect to employ an introducer sheath (not shown) as vascular access conduit for the CVAF 10. The presence of the filter member 16 at the distal end of the catheter body 12 creates a region of relatively lower flexibility and the practitioner may determine it beneficial to employ an introducer sheath for vascular access.

As used in this application, unless otherwise specifically stated, the terms "proximal" and "distal" are intended to refer to positions relative to the longitudinal axis of the catheter body 12. Those skilled in the art will understand that the catheter body 12 has a distal end which is first inserted into the patient and a proximal end which opposite the distal end. Additionally, the terms "inferior" or "inferiorly" are intended to refer to the anatomic orientation of being in a direction away from the patient's head while the terms "superior" or "superiorly" are intended to refer to the anatomic orientation of being toward the patient's head.

The multi-lumen aspect of the inventive central venous access filter catheter 10 is shown more clearly in FIGS. 2-5. The catheter body 12 has a proximal section 13 and a distal section 14 which is longitudinally opposite the proximal section 13, and which may have a relatively smaller diametric profile than the proximal section 13. As described above, the first lumen 44 terminates at the proximal port 32, while the second lumen 42 terminates at the distal port 34. A central guidewire lumen 30 may be provided that extends the entire longitudinal length of the catheter body 12 and terminates at the distal end of the catheter body 12 at a distal guidewire opening 31 that permits the catheter body to track along a guidewire during a procedure. The central guidewire lumen 30 may also be used to introduce fluids, such as bioactive agents, intravenous fluids or blood transfusions.

Additionally, at least one of a plurality of infusion lumens 40 are provided, each having at least one infusion port 36 that passes through a wall of the catheter body 12. Bioactive agents, flushing fluids for flushing or under elevated pressures for mechanical thrombolysis of thrombus in the filter member 16, contrast agents or other fluids may be infused through the infusion lumens 40 and out of the at least one infusion port 36 to pass into the patient's venous system for either local or systemic effect. In accordance with one embodiment of the invention, plural infusion ports 36 are provided with multiple ports 36 being provided in communication with a single infusion lumen 40 and spaced along a longitudinal axis of the catheter body 12. Additionally, plural infusion ports 36 may be provided in a circumferentially spaced manner to provide for fluid infusion at points spaced around the circumference of the catheter body 12. In this manner, fluid infusion is provided along both the longitudinal axis and the circumferential axis of the catheter body 12 within the spatial area defined by and bounded by the filter member 16. Because the plural infusion ports 36 communicate with the spatial area defined by and bounded by filter member 16, fluids introduced through the infusion lumens 40 are directed immediately at thrombus caught within the filter member 16. This permits thrombolytic agents, high pressure mechanical thrombolysis using a pressurized saline flush to be introduced directly to the situs of thrombus capture within filter member 16. Alternatively, thermal, ultrasound or other types of thrombolysis may be employed to disrupt thrombus captured by the filter member 16. For example, the annular space between the outer sheath 22 and the catheter body 12 may be used to introduce a thrombolytic to the filter and shower the filter to disrupt thrombus caught by the filter member 16. Additionally, the balloon depicted in FIGS. 21 and 22 may be positioned adjacent the filter member 16 and be provided with plural openings oriented in the direction of the filter member 16 to facilitate thrombolysis.

It will be understood, by those skilled in the art, that alternative arrangements of the first lumen 44, the second lumen 42, the guidewire lumen 30, or the infusion lumens are possible and contemplated by the present invention. The number and arrangement of lumens in the catheter body 12 is a function of the desired number of operable ports passing through the walls of the catheter body 12, the relative position of the operable ports, the desired position and geometry of the guidewire lumen 30, the desired longitudinal flexibility of the catheter body 12, the desirable degree of kink resistance of the catheter body 12, and other factors which are known to one of ordinary skill in the catheter arts.

While the present invention is not limited to specific dimensional sizes of either the catheter body member 12, the outer sheath 22, lumen diameter or port dimension, an exemplary outer diameter size of the outer sheath 22 is between 8 Fr (2.7 mm) and 9 Fr (3.0 mm) while an exemplary outer diameter size of the catheter member 12 is between 6 Fr (2.0 mm) and 7 Fr. A diametric transition taper 15 may be provided between the proximal portion 13 and the distal portion 14 of the catheter body 12 corresponding to the thickness of the filter member 16. In this manner, the outer surface of the filter member 16 is substantially co-planar with the outer diameter of the proximal portion 13 of the catheter body 12 about its entire circumference. Alternatively, the catheter body member 12 may have a constant diameter and the filter member 16 coupled to an outer surface of the catheter body member 12, with the outer sheath 22 having a luminal diameter sufficient to fit over the filter member 16. Moreover, the fixed first end 18 of filter 16 is positioned adjacent and in abutting relationship with the diametric transition 15, while the moveable second end 20 of filter member 16 is concentrically positioned around the distal section 14 of catheter body 12 and is reciprocally moveable thereupon to accommodate diametric expansion of the filter member 16. Lumen diameter and port dimension are a function of design requirements and are variable depending upon the desired purpose and function of the lumen or port, e.g., pressure sensing, infusion, evacuation, guidewire, flow sensing, or flow conduit.

In order to aid a physician in visualizing the CVAF 10 in vivo, at least one radio-opaque or other viewable marker may be provided. A first marker 24 is provided at the distal end of the outer sheath 22 and a second marker 36 may be provided at a distal tip 33 of the catheter body 12. It will be understood that when the outer sheath 22 is in its non-retracted delivery position, that the filter 16 will be covered and the marker 24 and the second marker 36 will be adjacent or in close proximity with one another. Alternatively, the outer sheath 22 may, itself, be made of or include a radio-opaque or other viewable material, such as a metal braid or metal reinforcement within or applied to a polymeric sheath. The first and second markers 24, 36 or the material of the outer sheath 22 may enhance visualization of the CVAF 10 under fluoroscopy, ultrasound or other visualization or guidance technique.

FIGS. 6-11 illustrate a second embodiment of the CVAF 50. Unlike CVAF 10, CVAF 50 does not include the central guidewire lumen 30 of CVAF 10. Rather, while the general construct of CVAF 50 is similar to that of CVAF 10, a different configuration of the inner lumens is employed.

CVAF 50, like CVAF 10, consists generally of a multi-lumen central venous access catheter body 12 having a proximal port 32 associated with a first lumen 54 and a distal port 34 associated with a second lumen 58, a filter member 16, having a fixed first end 18 and a moveable second end 20, is positioned generally intermediate the distal port 34 and the proximal port 32 and is generally concentric relative to the catheter body 12. Use of the term "generally intermediate" is intended to mean that at least a substantial portion of the filter member 16 resides intermediate the distal port 34 and the proximal port 32. Thus, the filter member 16 may partially overlay either or both of the proximal port 32 or the distal port 34.

The catheter body 12 has a proximal section 13 and distal section 14, which is longitudinally opposite the proximal section 13 which may have a relatively smaller diametric profile than the proximal section 13. As described above, the first lumen 54 terminates at the proximal port 32, while the second lumen 58 terminates at the distal port 34. An atraumatic tip 52 terminates the catheter body 12 at its distal end. The atraumatic tip 52 preferably includes a radio-opaque marker to aid in positional visualization of the distal end of the catheter body 12.

A plurality of infusion lumens 56 are provided, each having at least one infusion port 36, preferably plural infusion ports 36, that passes through a wall of the catheter body 12 and communicates with a space defined within an area bounded by the filter member 16. Bioactive agents, flushing fluids, pressurized mechanical thrombolytic fluids, or other fluids may be infused through the infusion lumens 56 and out of the at least one infusion port 36 to pass into the space defined by the filter member 16 and ultimately into the patient's venous system for either local or systemic effect. In accordance with one embodiment of the invention, the each of the plural infusion lumens 56 are in fluid communication with plural ports 36 arrayed along both the longitudinal axis and the circumferential axis of the catheter body. This configuration provides for fluid infusion along both the longitudinal axis and the circumferential axis of the catheter body 12 and in direct communication with the space defined by the filter member 16 that captures thrombus.

The infusion lumens 56, the first lumen 54 and the second lumen 58 are bounded by and separated from each other by first catheter septum 51 and second catheter septum 56 which also aid in providing structural support for the catheter body 12. First catheter septum 51 is a generally diametrically and longitudinally extending member that divides the first lumen 54 from the second lumen 58 along the longitudinal axis of the catheter body 12. Second catheter septum 56 may comprise a generally U-shaped member that intersects the first catheter septum 51 at a lower aspect of the septum and is connected with an inner wall surface of the catheter body 12 at upper aspects of the septum 51 to define two infusion lumens in lateral regions of the catheter body 12.

The filter member 16 has two general configurations. A first configuration consists generally of two opposing generally open conical sections formed by plural interconnected structural elements defining the lateral surfaces of each open conical section, wherein the two opposing generally open conical sections each have open bases facing each other which are interconnected by a generally cylindrical section of the filter member 16. Each open conical section has an open base and an apex, wherein the apices project in opposing directions, with one apex projecting proximally and another apex projecting distally relative to the axis of the catheter. The plural interconnected structural elements forming the lateral surfaces of each generally open conical sections may be strut-like structural members extending generally axially along the longitudinal axis of the filter member 16. The axially extending strut-like structural members may be linear members or may be curved members. The apices of each of the generally open conical sections are formed either of a generally cylindrical collar that serves to couple the filter member 16 to the catheter body 12. The generally cylindrical collar is concentrically engaged about the catheter body 12 and may be axially movable thereupon, or is formed by connections between adjacent pairs of longitudinal strut-like structural members which circumscribe a circumference of the catheter body 12. The generally cylindrical section of the filter member 16 is formed by a generally open lattice of interconnected structural elements which connect the base of a first open conical section to the base of a second open conical section. The generally cylindrical section of the filter member 16 lies in apposition with a vascular wall upon deployment of the filter member 16 with a vascular lumen.

A second general configuration of the filter member 16 consists generally of a single generally open conical section in which a plurality of longitudinal strut-like structural members form the lateral surfaces of the conical section and are connected to a generally cylindrical collar which couples the filter member 16 to the catheter body 12 at an apex of the generally open conical section. The base of the generally open conical section is formed by opposing ends of the longitudinal strut-like structural members. A generally cylindrical section of the filter member 16, formed of a generally open lattice of interconnected structural elements, extends from the longitudinal strut-like structural members forming the base of the generally open conical section, to provide a region of the filter member 16 which is in apposition to the vascular wall upon deployment of the filter member.

Figure 12:
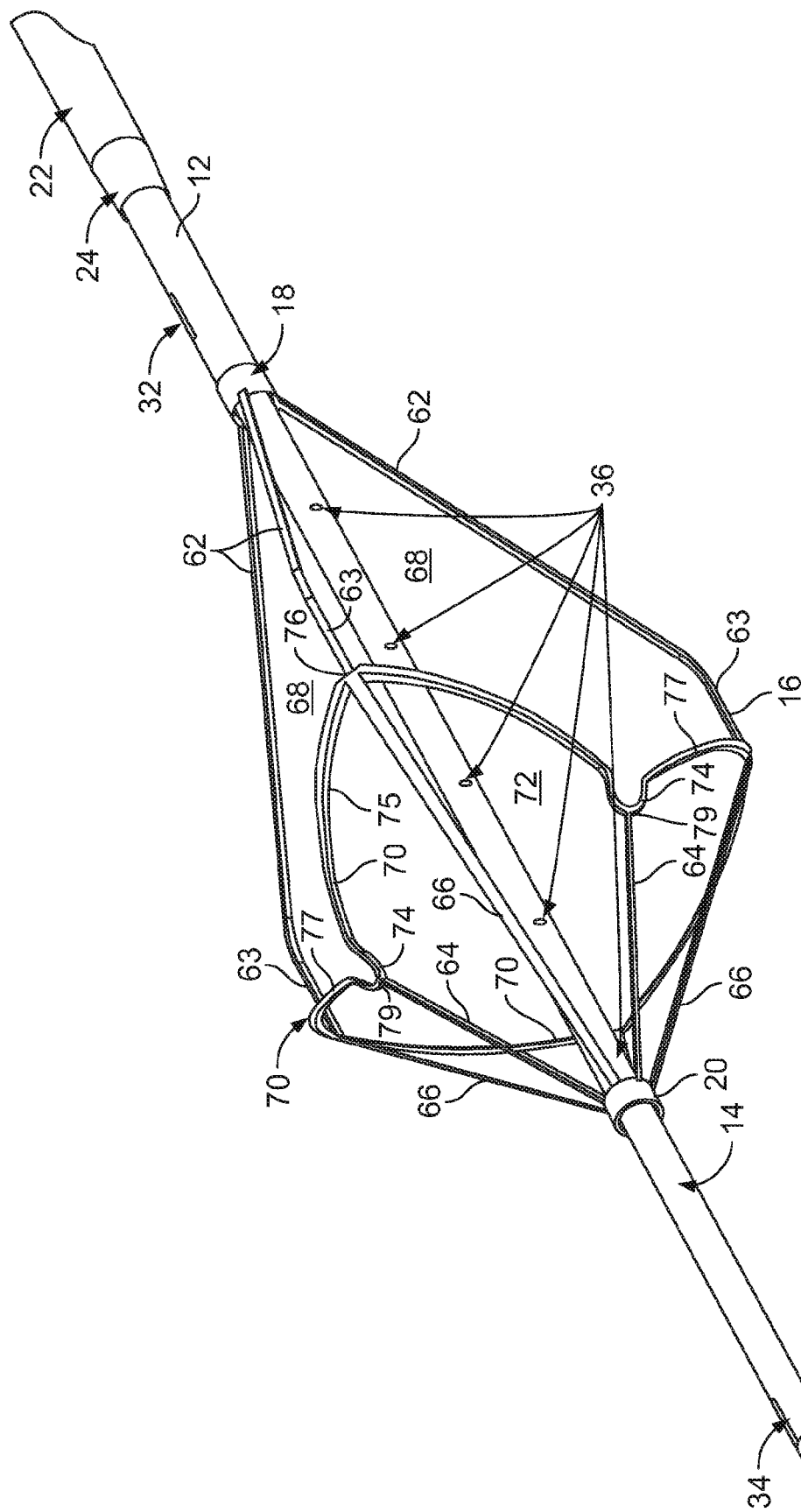
FIG. 12 is a perspective view of the central venous access vena cava filter catheter of FIG. 1 illustrating the vena cava filter in a diametrically expanded state.
Figure 15H:
FIG. 15A-15H are fragmentary side elevational views of the alternative embodiments of the vena cava filter member illustrated in FIGS. 14A-14H.
Figure 15G:
Figure 15F:
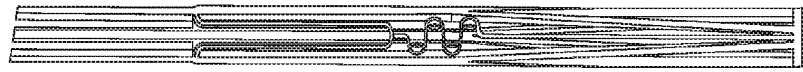
Figure 15E:
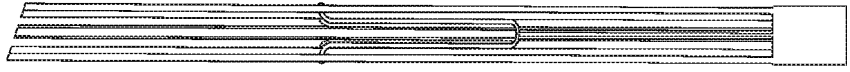
Figure 15D:
Figure 15C:
Figure 15B:
Figure 15A:

One embodiment of the filter member 16 is illustrated in its diametrically expanded configuration in FIGS. 12-13D. In this embodiment, filter member 16 consists generally of a first end 18 and a second end 20, each of which consists generally of a tubular structure which is circumferentially positioned about a section of the catheter body 12. One of the first end 18 and second end 20 are fixedly coupled to the catheter body 12, while the other is movable relative to the catheter body 12. At least one of a plurality of first strut members 62, are coupled at their first end to the first end 18 of filter member 16 and each extends axially relative to the longitudinal axis of the catheter body 12. Each of the first strut members 62 is an elongate member that, upon diametric expansion of the filter member 16, flares away from the central longitudinal axis of the catheter body 12, in a generally tapered conical manner, and terminates in an end section 63 that bends generally parallel to and along the longitudinal axis of the catheter body 12. A plurality of second strut members 64 are coupled at an end to the second end 20 of filter member 16 and each extends parallel relative to the longitudinal axis of the catheter body 12. A plurality of third strut members 66 are coupled at ends thereof to the an end of the filter member and each extends parallel relative to the longitudinal axis of the catheter body 12. It will be appreciated, by those skilled in the art, that the number of struts employed as the first strut members 62, the second strut members 64 and the third strut members 66 forming the filter member 16 may be evenly distributed about a 360 degree circumference and define the lateral wall surfaces of the filter member 16. A circumferential member 70 extends circumferentially to define a circumferential axis of the filter member 16 and has a series of continuous undulations defining peaks a series of peaks 75 and valleys 77 about the circumference of filter member 16. Each of the plurality of first strut members 62, the plurality of second strut members 64 and the plurality of third strut members 66 are coupled to the circumferential member 70 at different points about its circumferential axis and intermediate the proximal end 18 and the distal end 20 of the filter member 16. In its unexpanded state the filter member 16 has a generally tubular shape, while in its expanded state the filter member 16 assumes one of the general configurations discussed above, i.e., either oppositely extending generally open conical sections or a single generally open conical section.

The plurality of first strut members 62 are preferably offset from each other by approximately 120 degrees about the circumference of the catheter body 12. The plurality of second strut members 64 are also preferably offset from each other by approximately 120 degrees. Finally, the plurality of third strut members 66 are also preferably offset from each other by approximately 120 degrees. Each of the plurality of first strut members 62 couple at a junction 76 to the circumferential member 70 at a peak thereof. Similarly, each of the plurality of third strut members 66 couple at junction 76 to the circumferential member 70 at a peak thereof. In this manner, a first strut member 62 and a third strut member 66 are each coupled to circumferential member 70 at junction 76 and, in this relationship, form a generally linear member that extends along the longitudinal axis of the catheter body and connects between the proximal end 18 of the filter member 16 and the distal end 20 of the filter member 16. Each of the second strut members 64 couple, at their proximal ends to a valley 77 of the circumferential member 70 and connects at a junction 79. Unlike the connections at junction 76 between the plurality of first strut members 62 and the plurality of second strut members, in this embodiment of the filter member 16, there is no member that connects to junction 79 and extends from the first end 18 of the filter member 16. In this configuration, the circumferential member 70 assumes a generally circumferential tri-leaflet ring having three peaks 75 and three valleys 77 which circumferentially circumscribe a central opening 72 which faces inferiorly relative to the patient's blood flow such that the blood flow first passes into the central opening 72 and past the third strut members 66 and the second strut members 64 then past the first strut members 62.

To facilitate bending and folding of the circumferential member 70 between the expanded and unexpanded states, generally U-shaped hinge members 74 may be provided at each of the valleys 77 of the circumferential member 70. It will be understood that each of the plurality of first strut members 62, plurality of second strut members 64, plurality of third strut members 66 and the circumferential member 70 are preferably fabricated of biocompatible materials, such as shape memory alloys, superelastic materials or elastic materials, including, without limitation, titanium, vanadium, aluminum, nickel, tantalum, zirconium, chromium, silver, gold, silicon, magnesium, niobium, scandium, platinum, cobalt, palladium, manganese, molybdenum and alloys thereof, such as zirconium-titanium-tantalum alloys, cobalt-chromium-molybdenum alloys, nitinol, and stainless steel.

FIGS. 14A-14H and corresponding FIGS. 15A-15H depict alternative embodiments of the filter member 16, labeled 80, 90, 100, 110, 120, 130, 140 and 150, respectively. Like filter member 16, each of filter members 80, 90, 100, 110, 120, 130, 140 and 150 having a first end 18 and a second end 20 that each consist of a generally ring-like structure intended to circumferentially couple to a catheter body 12 (not shown), with the first end 18 being fixed and the second end 20 being reciprocally moveable axially along the distal portion 14 of catheter body 12. Like filter member 16, each of the alternative filter member embodiments depicted in FIGS. 14A-14H and 15A-15H, consist of a plurality of first strut members 81, 91, 101, 111, 121, 131, 141 and 151, respectively, extending distally from the first end 18 of the filter member and a plurality of second strut members 83, 93, 103, 113, 123, 133, 143 and 153, respectively, extending proximally from the distal end 20 of the filter member, with a diametrically expansible circumferential member 87, 97, 107, 117, 127, 137, 147, 157, respectively, interconnecting the distally extending strut members 81, 91, 101, 111, 121, 131, 141 and 151, respectively, with the proximally extending strut members 83, 93, 103, 113, 123, 133, 143 and 153. In the alternative embodiments of filter members 100, 110 and 120, at least some distally extending strut members and at least some of the proximally extending strut members form linear elements that extend along the entire longitudinal axis of the respective filter member, with the circumferential member being comprised of at least one undulating or serpentine ring structure.

In the alternative embodiments of filter members 80, 90, 130, 140 and 150, a plurality of distally extending strut members are provided spaced approximately 120 degrees apart from one and other about the circumference of the filter members, and the distally extending strut members bifurcating once or twice distally in a generally Y-shaped manner as in filter members 80, 130, 140 or 150, or the proximally extending strut members bifurcating proximally in a generally Y-shaped manner and interconnecting with the distally extending generally Y-shaped strut members to form a diamond-like pattern as in filter member 90. In filter members 90 and 140, the circumferential member is formed by the diamond-like pattern formed by the intersection of the plurality of struts. In contrast, in filter members 80, 130 and 150, the circumferential member is formed by at least one undulating or serpentine ring structure which is diametrically expansible. As illustrated in filter members 110, 120 and 130, apical portions of each undulating or serpentine ring structure is interconnected by an interconnecting member 114, 124, 134, respectively, either with an adjacent ring structure, as in filter member 110 or to a distal end 20 of the filter member itself A longitudinally serpentine section 132 in filter 32 may be provided in conjunction with the interconnecting member 134, to afford greater expansive properties to the circumferential member 137.

According to some embodiments particularly well-suited for placement by femoral or other infrarenal approach, the filter member 16 is characterized by a generally conical filter member 16 having a greater open surface area exposed to the flow of embolic material into the filter at its proximal end, while the distal end has smaller open surface area exposed to the flow of embolic material to capture the embolic material in the distal end of the filter member.

In other embodiments particularly well-suited for placement by a jugular or suprarenal approach, the filter member 16 is characterized by a generally conical filter member 16 having a greater open surface area exposed to the flow of embolic material into the filter at its distal end, which the proximal end of the filter member 16 has a smaller open surface area exposed to the flow to capture smaller embolic material in the distal end of the filter member 16.

Additionally, in all of the embodiments the filter member 16 is self-centering to provide proper apposition against the vascular walls and centering within the lumen of a blood vessel. This maximizes the flow dynamics of the filter member 16 within the blood vessel for purposes of capturing embolic material within the struts of the filter and centers the catheter body member 12 within the vascular lumen.

As noted above, the proximal 32 and distal 34 ports serve as means for measuring flow rates or pressure differentials across the filter 16. This may be accomplished by including flow sensors and/or pressure transducers 19 in operable association with each port 32, 34, with the associated electrical connections to the flow sensors an/or pressure transducers 19 passing through the respective lumens associated with each port 32, 34 and terminating at the proximal end of the catheter body 12. Where flow sensors 19 are employed, a single flow sensor associated with proximal port 32, the distal port 34 or the distal end of outer sheath 22 may be sufficient to detect fluid flow rate at the position of the catheter body 12. By providing a flow sensor at the distal end of sheath 22, the clinician will be able to determine flow velocity at the distal end of the outer sheath 22 prior to introducing the catheter body 12 and make fine adjustments to the placement of the distal end of the outer sheath 22 to ensure proper placement for the filter member 16. Plural flow sensors 19 may be employed and operably associated with each of proximal port 32 and distal port 34 to sense changes in flow velocity across the filter member 16. Alternatively, the flow sensors and/or pressure transducers 19 may reside in communication with the lumens respectively associated with each port 32, 34 at the proximal end of the catheter body 12, thereby eliminating the need for electrical connectors resident with the associated lumens. Furthermore, wireless flow sensors and/or pressure transducers may be provided in communication with each port 32, 34, and be operably coupled to a power source and a transmitter to wirelessly transmit telemetry data from the transducers to a wireless receiver in communication with the transmitter, as is known in the art.

Alternatively, the proximal 32 and distal ports 34 may be used for monitoring or sensing other conditions in the body that are detectable in the blood. For example, analyte sensors may be introduced to either the lumens communicating with the proximal 32 or distal ports 34 or to the ports themselves to monitor and/or sense chemical or biochemical conditions in the body. An example of this application is monitoring or sampling blood glucose levels for diabetes control. Further, the proximal 32 and distal ports 34 may be used for fluid infusion or for withdrawal or evacuation of fluids or other material through the catheter body 12. In this later instance, where the proximal port 32 is positioned to underlay the filter member 16, thrombus collected in the filter member 16 may capable of being lysed, either by thrombolysis through the infusion ports 36 or under the influence of thermal or mechanical lysis, such as by introducing a laser, ultrasound or other system capable of lysing thrombus, which may be introduced through the lumen communicating with the proximal port 32, or the distal port 32 or the guidewire lumen 30, or introduced separately from the CVAF 10, positioned within the space bounded by the filter member 16, lysing thrombus collected in the filter member 16 and evacuating the lysed thrombus through the proximal port 32

It is known that flow rate increases proximally within the venous system. For example a flow rate of 1 L/min is typical in one femoral vein, increases to 2 L/min in the inferior vena cava and increasing another 0.7 to 1 L/min proximate the renal veins. Knowing the typical flow velocities in vessels of different transverse cross-sectional areas, coupled with a flow sensor 19 associated with the multi-lumen catheter body 12 may serve to supplement or replace the requirements for fluoroscopy or sonography in placement of the CVAF 10, 50.

Other sensors, such as, for example, chemosensors, color sensors, electrical sensors or biosensors, may be employed in lieu of or in addition to pressure transducer and/or a flow sensor 19 in order to detect other changes or conditions within the patient's vasculature. For example, color sensors exist that sense color changes in thrombus, such color changes may be displayed and interpreted by the medical practitioner as an indication of thrombus staging. Analyte sensors, such a as a glucose sensor or an oxygen saturation sensor may also be employed.

The filter member 16, or its alternative embodiments described above, may be fixed to the catheter body 12 or may be removably coupled to the catheter body 12 for deployment as either a permanent filter or as a temporary and retrievable vena cava filter. Removable coupling of the filter member to the catheter body 12 may be accomplished with a variety of release and retrieval mechanisms operably associated the catheter body 12 and proximate the diametric transition 15. Non-limiting examples of such release and retrieval mechanisms include a wire release that engages with a the first end 18 of the filter, a cooperating indexed detent and projection interaction between the catheter body 12 and the first end 18 of the filter, such as a detent in the proximal end of the filter and a cooperating projection in the multi-lumen catheter that is positionally indexed to the detent and releasable from the detent, or, alternatively, a helical slot or threads may be formed in the proximal end 18 of the filter and indexed and cooperating projection in the multi-lumen catheter than permits engagement and disengagement with the helical slot or threads.

In use, an introducer sheath may or may not be used, and when the introducer sheath is first placed into the body in a normal manner for introducing a central venous line, such as by the Seldinger technique. Specifically, after accessing a vein using a large bore needle, under local anesthesia, a guidewire is inserted through the needle bore and passed into the vein. Once the guidewire is positioned, the needle is withdrawn, and a dilator together with the introducer sheath introduced over the guidewire. Once the introducer sheath is positioned at a desired location within the venous system under radiography, the dilator may be removed from the patient. Radiopaque markers associated with the introducer sheath may be employed to assist in positional visualization of the distal end of the introducer sheath. The outer sheath 22 covering the filter 16 is removed while introducing the filter member 16 and catheter body 12 into the introducer sheath. The outer sheath 22 constrains the filter member 16 during its passage through the introducer sheath and positioning the distal end of the catheter within the patient's vasculature. Once the distal end of the catheter body 12 reaches the distal end of the introducer sheath, the filter is deployed. If the filter therapy alone is desired, the filter member 16 is detached from the catheter body 12 and the catheter body 12, introducer sheath and guidewire is withdrawn from the patient. Where both central venous access and filter therapy is desired, the introducer sheath and catheter body 12 with the filter member 16 is left in the patient until withdrawal is required.

Retrieval and removal of a detached filter member 16 is accomplished using a second procedure under local anesthesia which substantially replicates the placement of the CVAF, with a capture sheath (not shown), similar to introducer sheath, being introduced, a retrieval catheter being introduced through the sheath, and engaging the filter member 16, then withdrawn into the capture sheath to collapse the filter member 16, with the entire assembly of the filter member 16, catheter body 12, outer sheath 22 and guidewire, if used, is withdrawn from the patient.

As depicted in FIGS. 16A and 16B, which depict the undeployed state (FIG. 16A) and the deployed state (FIG. 16B) of the filter member 216, respectively, common to each of the embodiments of the present invention 200 is an inner catheter 214 that carries the vena cava filter 216 at a distal end thereof. The inner catheter 214 is concentrically and reciprocally engaged within an outer sheath 222 such that relative axial movement of the inner catheter 214 and the outer sheath 222 either exposes the vena cava filter 216 for deployment or captures the vena cava filter 216 for retrieval. A first hub member 225 is coupled to a proximal end of the outer sheath 222 and a second hub member 227 is coupled to a proximal end of the inner catheter 214. First hub member 225 and second hub member 227 are engageable, such as by a threaded, bayonet, snap fit, friction fit or interference fit fitting, to secure the inner catheter 214 within the outer sheath 222 and restrict relative axial movement of the two elements after deployment of the vena cava filter 216. A flush line 229 communicates with the first hub member 225 and is in fluid communication with a luminal space within the outer sheath 222. A plurality of fluid lines 231, 233, 235, 237 communicate with the second hub member 227 and are each in fluid communication with one of the plural lumens within the inner catheter member 214, e.g., lumens communicating with the proximal, distal or infusion ports (not shown). A distal tip 26 is provided at a distal end of the inner catheter.

A jugular approach necessitates that the catheter be introduced retrograde relative to the vector of blood flow within the vena cava, i.e., the catheter is introduced through the jugular vein and directed inferiorly toward an infrarenal position. Additionally, since the blood flow opposes the distal end of the catheter and passes toward the proximal end, the vena cava filter must open inferiorly such that its largest diametric section in apposition to the vessel walls opens toward the distal end of the catheter rather than toward the proximal end of the catheter as with the femoral approach.

Figure 17:
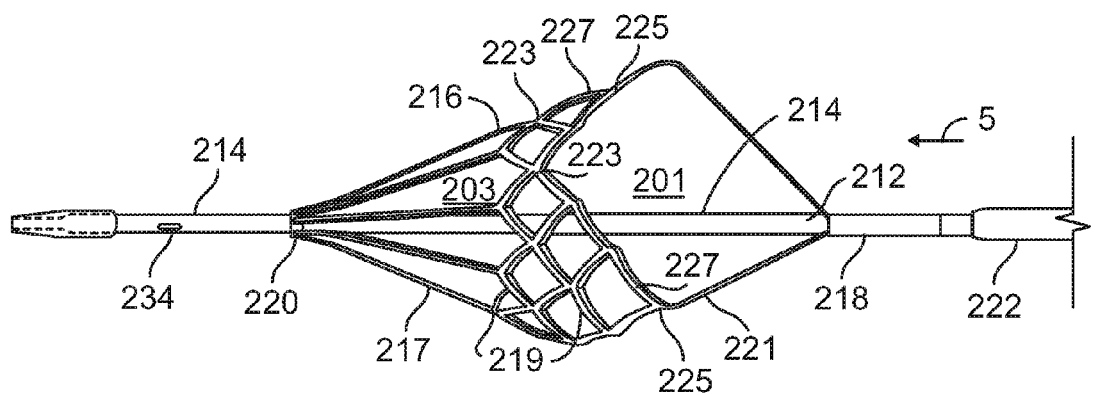
FIG. 17 is a side elevational view of an vena cava filter member in its expanded state in accordance with one embodiment of the present invention.
Figure 18:
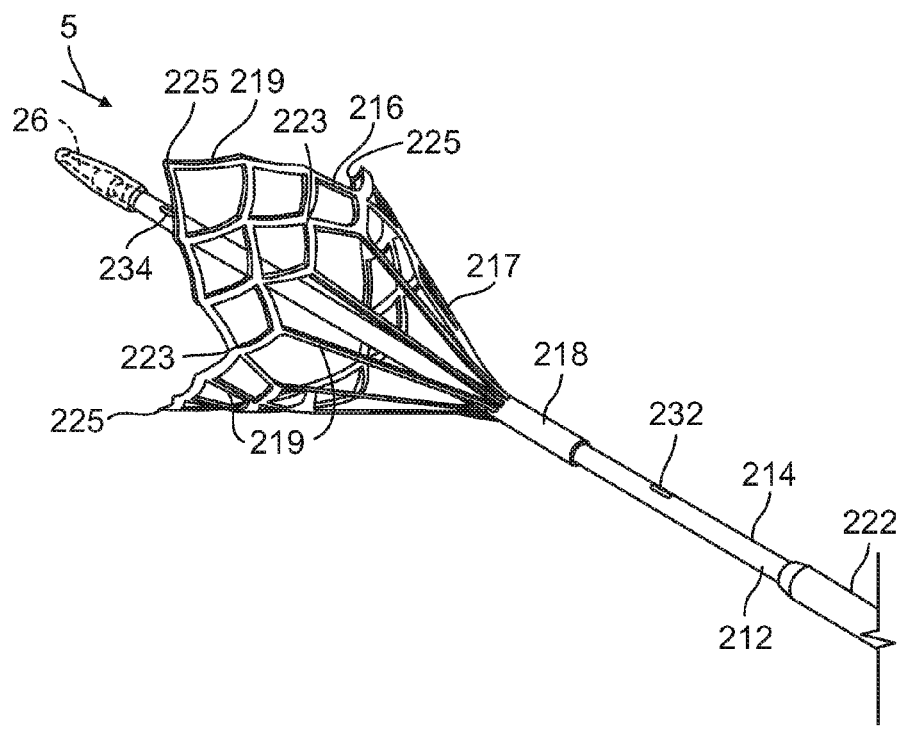
FIG. 18 is a perspective view of a vena cava filter member in its expanded state in accordance with an alternative embodiment of the present invention.
Figure 19:
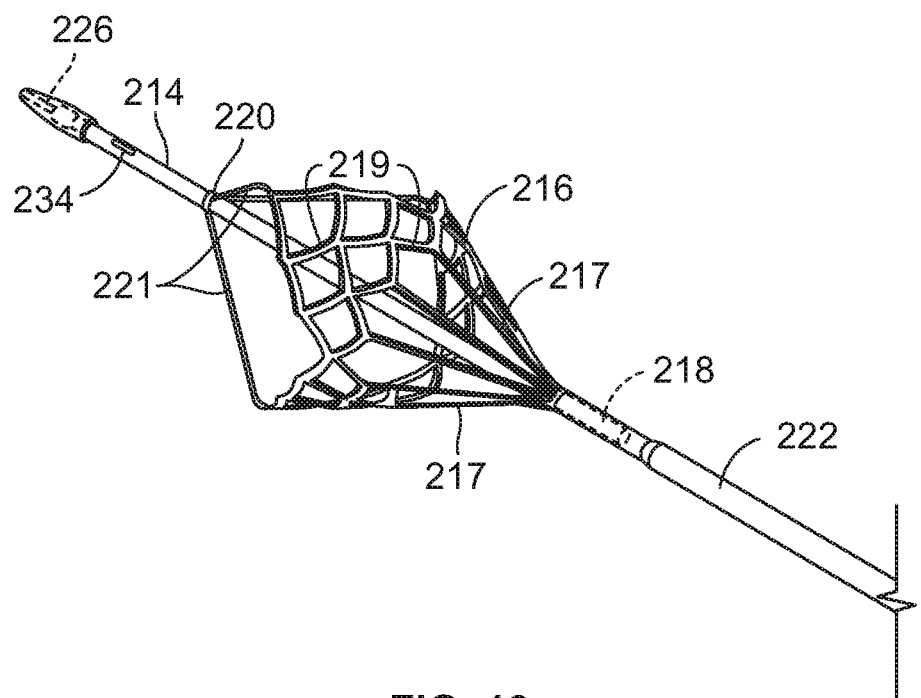
FIG. 19 is a perspective view of a vena cava filter member in its expanded state in accordance with yet another embodiment of the present invention.
Figure 20:
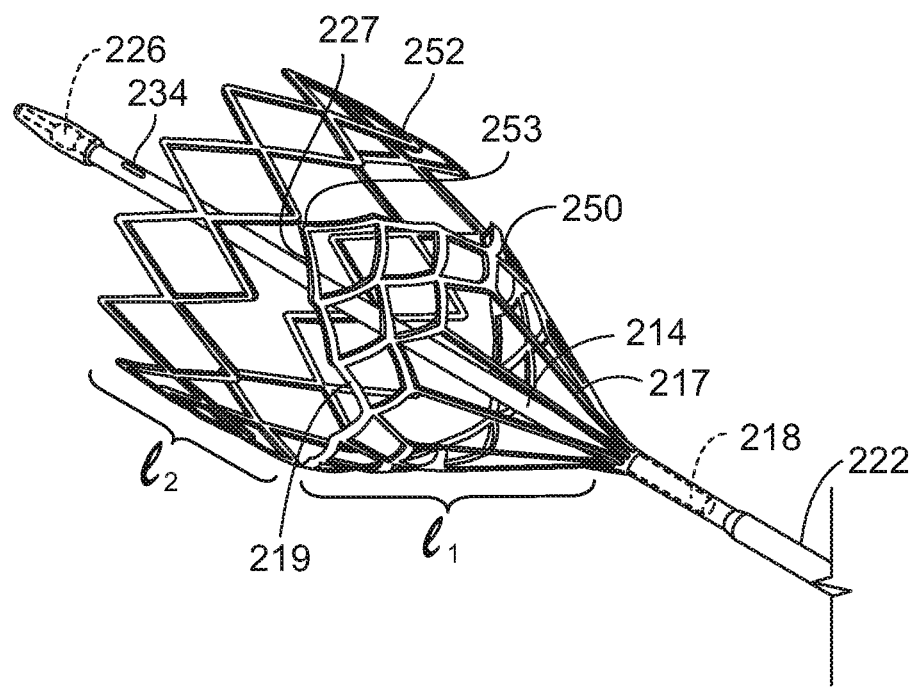
FIG. 20 is a perspective view of a vena cava filter member in its expanded state in accordance with still another embodiment of the present invention

FIGS. 17-20 depict alternative embodiments of vena cava filter members in accordance with the present invention. FIG. 17 illustrates a filter orientation for a femoral approach, while FIGS. 18-20 illustrate a filter orientation for a jugular approach. As illustrated in FIG. 17, filter member 216 defines a relatively larger volume open space 201 and a relatively smaller volume open space 203. Open spaces 201 and 203 are bounded by structural members of the filter member 216 and are both open toward the direction of blood flow indicated by arrow 5, with larger open space 201 being relatively upstream the blood flow relative to smaller open space 203 in both the femoral or the jugular orientation of filter member 216.

As with all previous embodiments described of the filter member, filter member 216 is formed of plural interconnected structural elements. In accordance with the preferred embodiments of the filter members of the present invention, and as particularly exemplified by filter member 216, the filter member has a first end 218 and a second end 220, at least one of which is attached to the distal section 214 of the catheter body 212. First structural members 217 extend generally axially, either proximally as shown in FIG. 17 or distally as shown in FIG. 18, along the longitudinal axis of the filter member 216. Again, it is understood that use of the terms "proximal" or "proximally" and "distal" or "distally" are intended to refer to positions relative to the longitudinal axis of the catheter body 212. The first structural members 217 are connected to either the first end 218 or the second end 220 of the filter member 216. Second structural members 219 are connected to the first structural members 217 at an end of the first structural members 217 which is opposite that connected to either the first end 218 or the second end 220 of the filter member 216. In accordance with a preferred embodiment of the invention, the second structural members 219 form at least two successive zigzag shaped structures which are connected to an end of the first structural members and at opposing apices 223 to form conjoined ring-like structures about the circumference of the filter member 216. In this manner the second structural members 219 generally define lattice-like pattern upon diametric expansion of the filter member 216. The lattice-like pattern formed by the second structural members 219 projects axially along the longitudinal axis of the catheter 214 tapering to form at least one petal-like projection 225 that terminates in a terminal apex member 227. As will be appreciated by those skilled in the art, FIG. 17 depicts three petal like projections 225, with one being behind the plane of the figure and, therefore, not shown. Each of the petal-like projections 225 act to engage and oppose vascular wall surfaces to seat the filter member 216 against the vessel wall, and center the filter member and catheter 214 within the vascular lumen. As illustrated in FIG. 17, third structural members 221 are provided and are connected to each of the terminal apex members 227 and extend axially relative to the catheter 214 and connect with a second end 218 of the filter member 216.

In the embodiment illustrated in FIG. 17, which is an orientation of the filter member 216 for a femoral approach, and in the embodiment illustrated in FIG. 19, which is an orientation of the filter member 216 for a jugular approach, the first end 218 of the filter member 216 is fixedly connected to the catheter 212, while the second end 220 of the filter member 216 is movably coupled to the catheter 212 and moves axially along the catheter 216 upon expansion or contraction of the filter member 216.

FIG. 18 depicts an embodiment of the filter member 216 identical to that illustrated in FIG. 19, with the sole exception that the third structural members 219 and the second end 220 of the filter member 216 are omitted. In this embodiment, the terminal apex member 227 of each petal-like member 225 are not connected to a second end 220 of the filter member 216 by the third structural members 219.

FIG. 20 depicts an alternative embodiment of the filter member 216 which is similar to that depicted in FIG. 18, except that at least one circumferential ring member 252 is connected to the terminal apex member 227 of each of the petal-like members 225 at a juncture 253 with the terminal apex member 227. The addition of the additional circumferential ring member 252 results in a relative elongation over the length L1 of the filter member 216 depicted in FIG. 18 by a length L2 which facilitates additional apposition between the filter member 216 and the vascular wall and stabilization of the petal-like members 225.

Figure 21A:
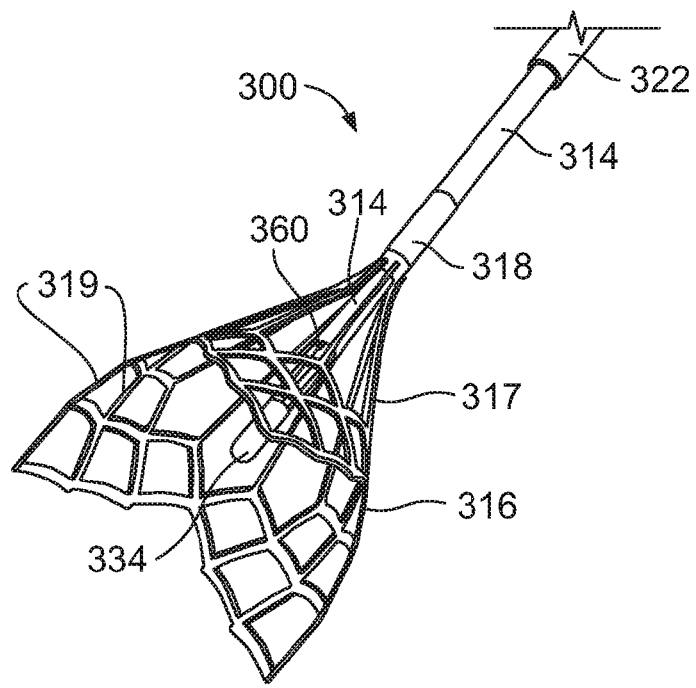
FIGS. 21A and 21B are perspective views of a vena cava filter member mounted at a distal end of a central line catheter having a distal balloon.
Figure 21B:
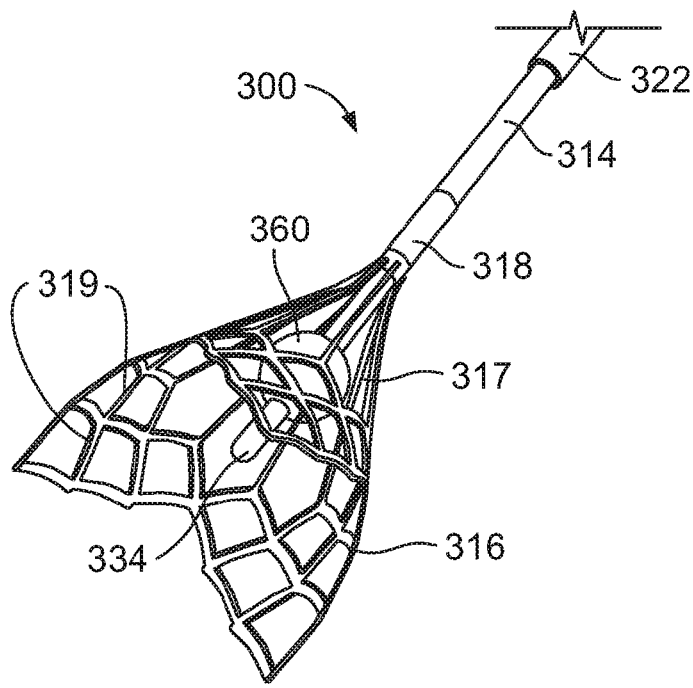

FIGS. 21A and 21B depict an alternative embodiment of the filter member 216 in FIG. 18, having first end 318, first structural elements 317 and second structural elements 319 all analogously arranged as in the embodiment of FIG. 18. Filter member 300, however, employs a modified distal end 314 of the catheter 312 to include an expansive balloon 360. The guidewire lumen of the multi-lumen catheter 312 may be used in place of a distal port for either condition sensing, flushing, infusion or the like. The expansive balloon 360 may be used to break up thrombus captured within the filter member 316, either by mechanical force through serial dilatation or by infusion of a thrombolytic agent through openings in the balloon 360. FIG. 21A depicts the balloon 360 in its collapsed state, whereas FIG. 21B depicts the balloon in its expanded state.

Alternatively, an expansive balloon 360 may be placed proximal the filter member 300 and serve to temporarily occlude the vessel to facilitate aspiration or evacuation of thrombus from the filter member 30 for a femoral orientation.

Figure 22A:
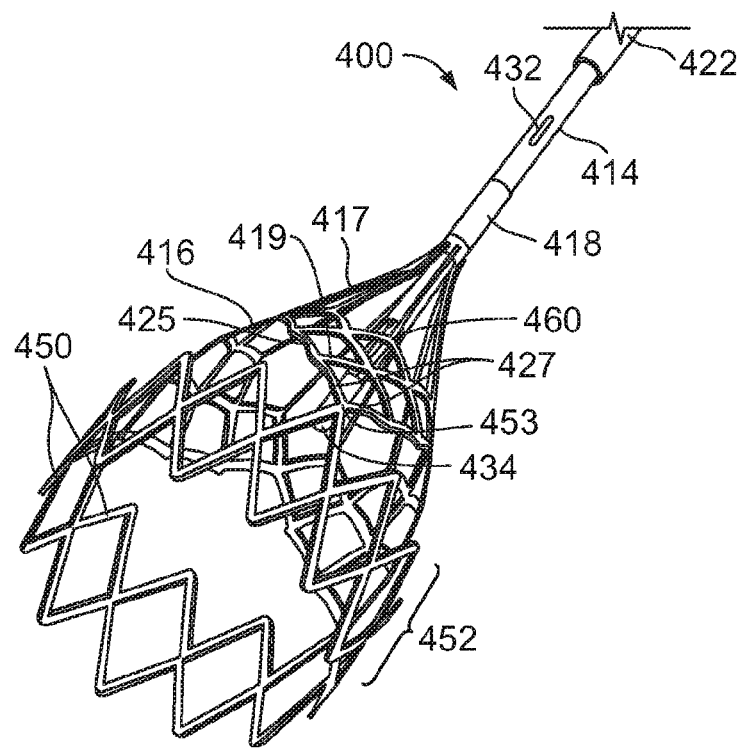
FIGS. 22A and 22B are perspective views of an alternative embodiment of a vena cava filter member mounted at a distal end of a central line catheter having a distal balloon.
Figure 22B:
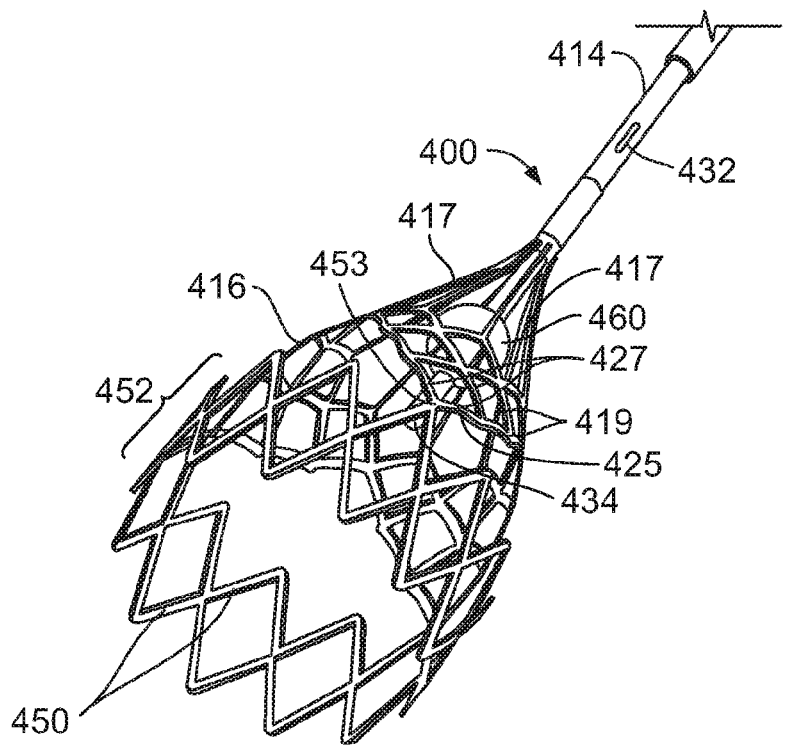

Finally, FIGS. 22A and 22B depict an alternative embodiment of the filter member 216 in FIG. 20 having first end 418, first structural elements 417 and second structural elements 419, at least one circumferential ring member 452 connected to the terminal apex member 427 of each of the petal-like members 425 at a juncture 453 with the terminal apex member 427; all analogously arranged as in the embodiment of FIG. 20. Filter member 400, however, employs a modified distal end 414 of the catheter 412 to include an expansive balloon 460. The guidewire lumen of the multi-lumen catheter 412 may be used in place of a distal port for either condition sensing, flushing, infusion or the like. The expansive balloon 460 may be used to break up thrombus captured within the filter member 416, either by mechanical force through serial dilatation or by infusion of a thrombolytic agent through openings in the balloon 460. FIG. 22A depicts the balloon 460 in its collapsed state, whereas FIG. 22B depicts the balloon in its expanded state.

Again, an expansive balloon 460 may be positioned proximal the filter member 416 to permit temporary occlusion of the blood vessel and permit aspiration or evacuation of thrombus from the filter member 416 for a femoral orientation.

It will be appreciated by those skilled in the art that in all embodiments of the described central venous access filter, the filter member has a relatively larger opening that is open inferiorly in a direction that opposes the blood flow vector and employs structural elements that taper superiorly along the direction of the blood flow vector to reduce the open surface area of the filter member and capture thrombus.

Thus there has been described a central venous access filter in accordance with the foregoing embodiments of the invention which include, generally, a multi-lumen catheter body, a filter member and an introducer sheath. The multi-lumen catheter body has a plurality of ports each of which are in fluid flow communication with at least one lumen in the multi-lumen catheter body. Lumens may include a central guidewire lumen useful for tracking over a guidewire and/or larger volume infusion of bioactive agents, intravenous fluids, blood transfusions, or other fluids; infusion lumens in communication with infusion ports positioned to direct fluids to the space bounded by the filter member for introducing bioactive agents, including thrombolytic agents or flushing agents, including pressurized fluids for mechanical thrombolysis directly to the capture site of the thrombus in the filter member; and lumens communicating with proximal and distal ports which may also be used for fluid introduction and/or may house or communicate with sensors, such as pressure transducers, flow sensors, analyte sensors, color sensors, optical sensors or the like. The filter member may be detachable from the multi-lumen catheter body to permit temporary filter placement and later retrieval by a detachment mechanism that cooperates between the filter and the multi-lumen catheter body.

Clot Management Devices and Techniques

Below are described clot management devices and techniques, whereby when the filter is burdened with clots or thrombi, the clot management devices and techniques may be coupled with the multi-lumen catheter body, sheath, and filter to unburden the filter and permit catheter removal. Any of the clot management device and techniques may be combined with each and other and be included as a combination device or method for the filter monitoring, Temporary Dilator, Compliant Outer Sheath for Embolectomy, Basket or Guidewire to capture debris, Method for Clot Lysis, Thrombolytic Scaffold, Mechanical Thrombolytic Filter, Clot Detection Wires, or Device Removal Technique for Large Clots. The clot management devices and methods manage the filter in the expanded state burdened with clot or thrombi, such that, the filter may be removed from the body and contracted to the contracted state without the clot or thrombi being released downstream or distally from the filter during removal.

Filter Monitoring:

Monitoring the status of the filter in terms of clot capturing is one of the functions of the clot management techniques for the vena cava filter and also allows monitoring for deposits of clots into the filter. The results of this monitoring will influence two aspects of the patient management: (1) Administration of lytics and pressure infusion of solutions with the goal of breaking the clots; or (2) Evaluate the filter before filter removal to be able to recommend removal without further testing or to recommend an imaging study such us a CT venogram or alternate acceptable imaging means in the case of clot documentation.

The vena cava filter monitors the status of the filter regarding the percentage of the filter that is obstructed by clot based in hemodynamic monitoring by pressure ports in the proximal and distal area of the filter, as described above. Clinical data collected with other filters reveals that there is a gradient pressure developing as the filter becomes obstructed with clots. The magnitude of these changes is variable and depends on several factors including: IVC size, volume of clot, filter design, and the like. The pressure monitoring will generate waveforms via external pressure sensors. Signals generated by pressure and flow sensors may evaluate the gradient and the area under the waveform curve in conditions of changing intrathoracic pressure (inspiration/expiration) when the flow is changing and subsequently any changes in the pressures are more evident. In this way, knowing the distance between the two ports, the approximate equal size of the vena cava in both areas and the area under the curve during the negative intrathoracic pressure cycle, an area that could represent the approximate obstruction of the filter may be obtained.

Flow, temperature and pressure sensors may evaluate the status of the filter, as indicated above. The sensors may be positioned at various locations of the filter. Or the sensors are located in the distal end of the filter/catheter, which will provide another set of data that will be useful in determining the status of the filter.

Another method to evaluate the presence of clots in the filter comprises measuring cardiac output with thermodilution. Thermodilution comprises adding a fix volume of fluid at a constant rate and temperature through the proximal port in the filter to generate a change in the flow and temperature measured in the distal end of the filter. The changes in flow and temperature measured will be different according to the status (percentage obstructed) of the filter with a slower flow and change in temperature reflecting potential obstruction of the filter, and a faster flow reflecting an unobstructed filter. These results will be then compared to the baseline or recommended flows and temperatures for filters with no obstruction.

In one embodiment, the continuous flow sensor outputs may be interpreted without the requirements of volume injections. After immediate placement, the filter and sensors will generate information regarding the flow magnitude and wave forms, and then in the event of clot trapping the variations and differences in the flow patterns, whereby the variations and differences in flow pattern provide information to determine clot obstruction inside the filter. The use of integrated flow/pressure sensors may allow having the filter in a lower profile catheter as well as monitors to display the respective sensor data output from the filter.

Finally, the addition of pressure and flow sensors to this catheter which is placed in the inferior vena cava provides hemodynamic data about the patient. The most common indications for the filter will be in critical ill patients and this set of information will provide data of significant use for patients in which the hemodynamic and fluid monitoring are vital. Several observations that may be evaluated in an experimental fashion are shown in Table 1.

TABLE 1

|  | Flow Rate | Flow reversal vs. continuous | Central Venous Pressure |
| --- | --- | --- | --- |
| Hypovolemic Shock | Normal | Yes | Low |
| Right Heart Failure/PPH | Low | Yes | High |
| Septic Shock | High | No | Low |
| Cardiogenic Shock | Low | Yes | High |

Flow monitoring in the vena cava has been evaluated by echocardiography as a surrogate of pulmonary pressures and cardiac output. The combination of continuous pressure and flow monitoring adds important data for management of patients and clot management of the filter.

Figure 23A:
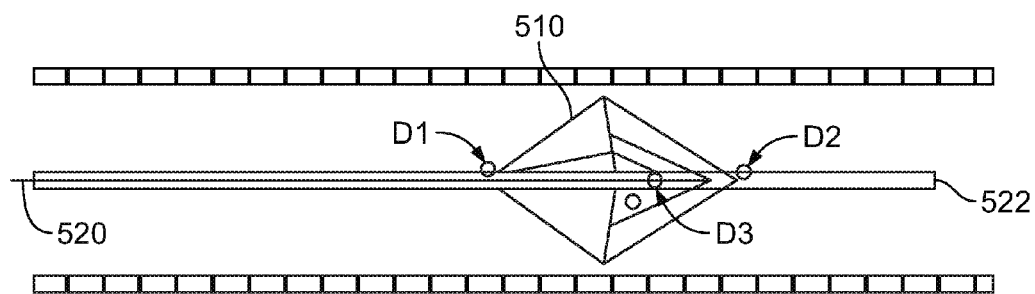
FIGS. 23A-23B are cross-sectional views of Optical Coherence Tomography/Doppler Flow using optical fibers or fiber within the filter to view clot.
Figure 23B:
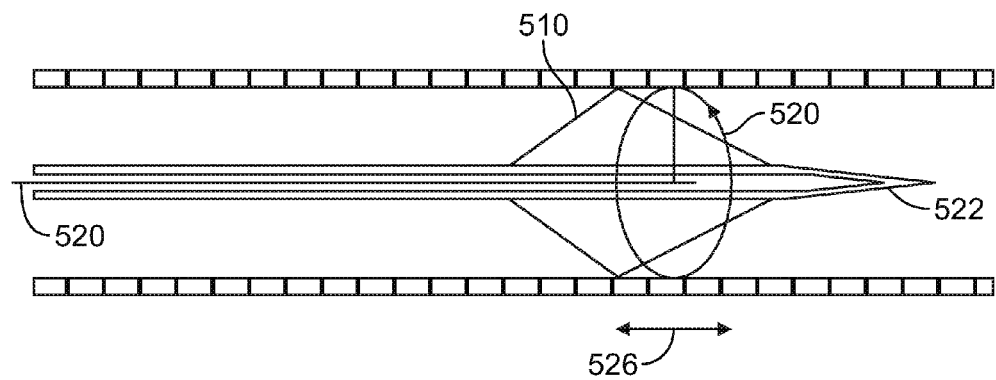

Alternatively, the use of fiber optic catheters 520 may detect a blood clot or monitor the filter 510 status be either direct optical visualization and/or Doppler measurement, as shown in FIGS. 23A-23B. Either embedded fibers 520 in the presence of at least one lumen or an additional Optical Coherence Tomography (OCT) catheter or optical fiber down the central lumen of the catheter 522 for radial visualization. The OCT modality may be the one as described in commonly owned U.S. patent application Ser. No. 13/735,810, filed Jan. 2, 2013, herein incorporated by reference in its entirety. Doppler measurement can rely on blood flow change at points D1, D2, and D3 along the catheter fiber or by measuring Doppler differential, as shown in FIG. 23A. The OCT or Doppler measurement may be more sensitive than current electronic or nanometer systems. OCT radiation 522 can measure both movement 526 and image the clot in the filter 510, as shown in FIG. 23B. The glass fiber may be allow for a simpler and cost effective system than metal wires to allow for single or multiple Doppler measurements may be taken, single or multiple A-line images and measurements, radial images or flow measurements, particle size analysis, and analyte analysis.

Temporary Dilator

Figure 24A:
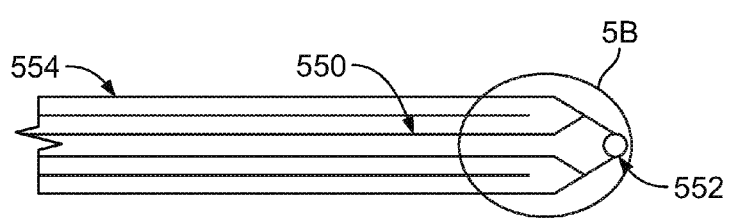
Figure 24B:
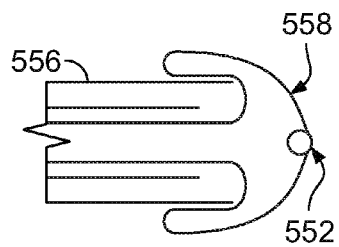

In one embodiment, a temporary dilator 550 longitudinally runs through the at least one lumen of the multilumen catheter body 554 for the entire length of the multilumen catheter body 554, as shown in FIG. 24A. The temporary dilator may be deployed to increase a central lumen of the catheter as to allow a filter burdened with a clot to be retrieved within the outer sheath, as the filter burdened with clot may increase the unexpanded state of the filter. The temporary dilator 550 has an inner lumen 552 that is sized appropriately for guide wire to be coaxially placed within the inner lumen 552. The distal tip of the temporary dilator allows for easy insertion of the device, such as a conical or angled distal tip. The temporary dilator 550 provides a smooth transition at the distal end of the sheath 556, as shown in FIG. 24B. After device is positioned in proper target site (e.g. infrarenal position), temporary dilator 550 would be removed and filter 560 would be deployed, as shown in FIG. 24C. The dilator 550 may decrease in diameter 559a when moved distally, to allow for removal of the dilator 550, as shown in FIG. 24D. Alternatively, the dilator 550 may decrease in diameter 559b when the dilator is moved proximally in an umbrella like fashion, such that the distal end of the dilator 550 folds over itself for removal, as shown in FIG. 24E. Alternatively, the dilator 550 is in place during insertion and deployment of the filter, as shown in FIG. 24F. After the filter is deployed, the dilator can be removed from the catheter. The resulting larger central lumen can be used for administration of large fluid volumes/high flow rates or for retrieval of filter with or without thrombus. The resulting catheter has a larger central lumen when the dilator is removed; therefore if thrombus is present during filter retrieval, dependent on size, it would be possible to capture more of the thrombus within the outer sheath 556. By having a temporary dilator for this purpose the device can benefit from higher flow rates and increased space for clot retrieval. The temporary dilator could be made of any flexible, low friction material. The dilator tip could be made of alternate materials to improve ease of access and to be atraumatic.

Compliant Outer Sheath for Embolectomy

Figure 25B:
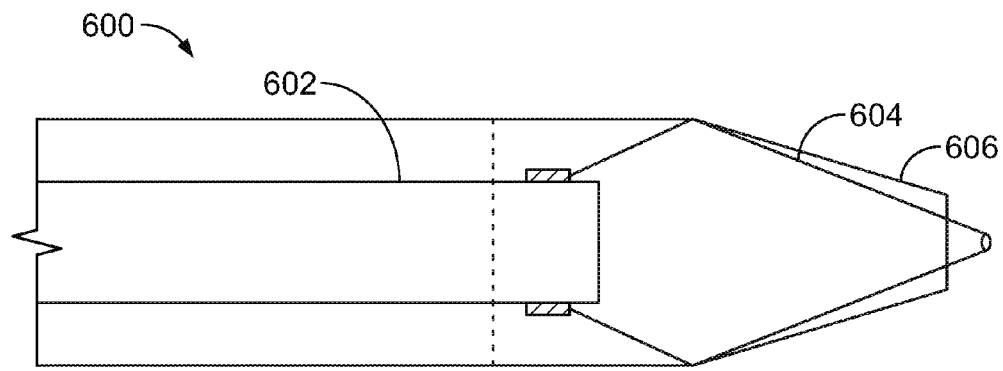
Figure 25C:
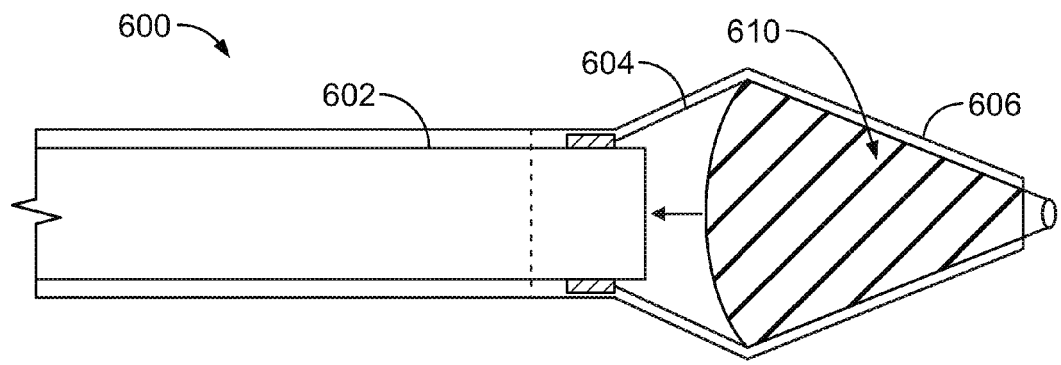
Figure 25D:
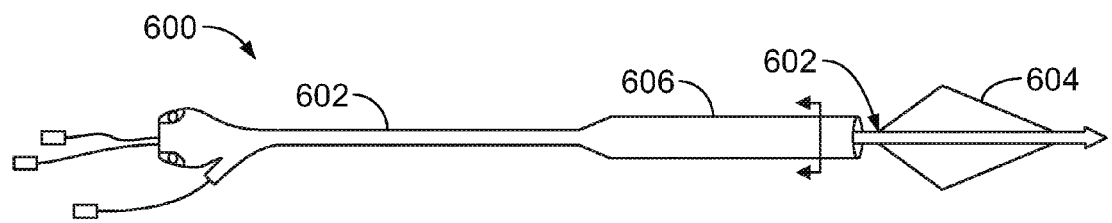
FIGS. 25D-25N are side views of multiple embodiments of the expandable sheath.

In one embodiment, the catheter 600 consisting of a single or multi-lumen inner shaft 602, as described previously, that has a filter 604 attached at its distal end, as shown in FIG. 25A. The filter 604 has an elongated distal basket 604a to comply with a "maximum" size blood clot. The distal tip of the filter 604 is encapsulated in a plastic and has a smooth transition with a compliant outer sheath 606. The compliant outer sheath 606 comprises a lumen through which the multilumen body 602 is disposed and the compliant outer sheath 606 is expandable. The compliant outer sheath 606 constrains the filter 604 and maintains its original dimensions when a thrombus is not present within the basket of the filter 604, as shown in FIG. 25B. When a thrombus 610 is present during retraction of the filter 604, the compliant outer sheath 606 expands over and stretches over the contracted state of the filter 604 and constricts the clot 610 into the single lumen inner shaft 602 and/or the inner area of the filter 604, as shown in FIG. 25C.

An expandable sheath may be included as an alternative embodiment, as shown in FIGS. 25D-25N. The integrated expandable sheath provides a minimally invasive method and assembly to remove clot 610 burdened filters. The expandable sheath includes a lower access profile provides the ability to expand to capture a clot 610 burdened filter 604. Retrieval systems for current filters are all larger that their deliver systems. The design of the expandable sheath reduces the amount of clot that is released during retrieval of the filter, as it expands to accommodate the larger diameter of the filter.

Figure 25E:
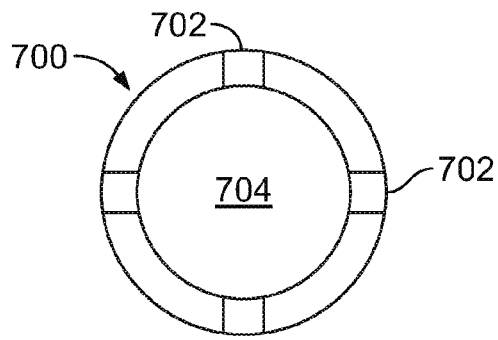
Figure 25F:
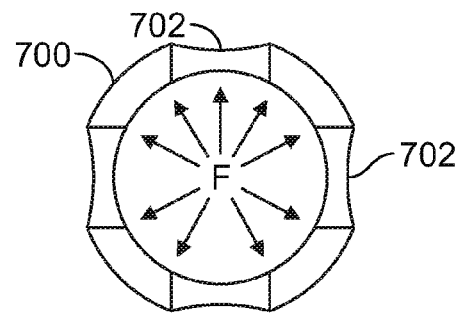

In one embodiment, the expandable sheath 606b comprises an extrusion tube 700 including a lumen 704 therein, wherein the outer wall of the expandable sheath 606b includes varying circumferential elastic properties around the circumference of the extrusion tube 700, as shown in FIGS. 25E-25F. The extrusion tube 700 includes a plurality of longitudinal stripes 702 around the circumference of the extrusion tube 700 and the plurality of longitudinal stripes run the length of the extrusion tube 700 from the proximal end to the distal end. Alternatively, the plurality of longitudinal strips 702 may be disposed only along a portion of the distal end of the extrusion tube 700 that is to expand around the clot burdened filter in the expanded and contracted state. Alternatively, one or more of the longitudinal strips 702 may include an alternate stripe material that is more elastic in nature than the main body material of the extrusion tube 700, which further allows the tube 700 to expand when an outward radial force F is being applied (as shown in FIG. 25F). The expansion of the longitudinal stripes 702 allow a clot burdened filter to be retrieved into the lumen 704 of the extrusion tube 700. Varying number of longitudinal stripes could be used to control the radial forces that are required to expand the sheath (e.g. a greater number of longitudinal stripes 702 may be employed for a greater lumen 704 expansion of the extrusion tube 700). In one embodiment, the extrusion tube 700 includes at least four longitudinal stripes 702 equidistant along the circumference of the extrusion tube 700. Alternatively, the longitudinal stripes 702 may be positioned at different distances from each other along the circumference of the extrusion tube 700. For example, one or more of the longitudinal stripes may be positioned at the top or bottom of the extrusion tube 700. The extrusion tube includes outer and inner surfaces to be smooth in the unexpanded state. If a clot burdened filter is retrieved into the expandable sheath, the elasticity of the design would cause the distal end to recover to its original diameter size of the lumen 704.

Figure 25G:
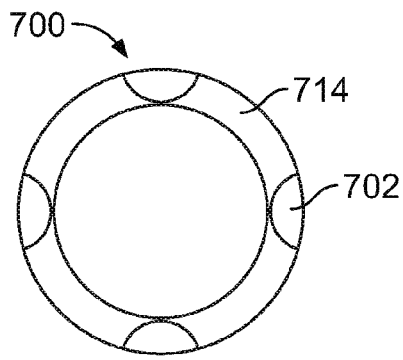
Figure 25H:
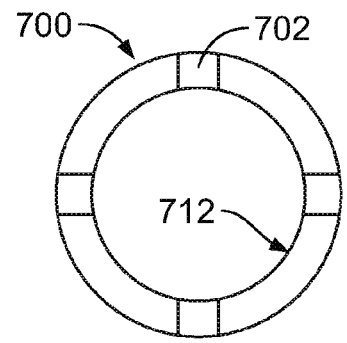
Figure 25I:
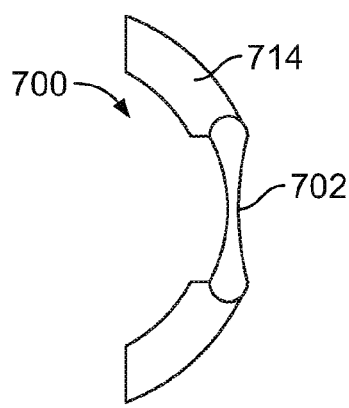
Figure 25J:
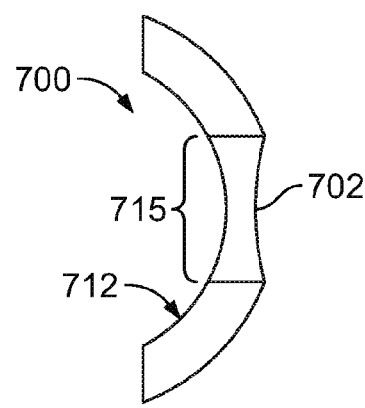

In an alternative embodiment, the expandable sheath includes an internal liner 712, an external liner 712, or an integral liner 714 to control the expansion force of the expandable sheath, as shown in FIGS. 25G-25H. The internal liner or external liner 712 may be a thin walled tube on the inner wall surface or the outer wall surface of the extrusion tube, which may be PFTE or other polymer material, as shown in FIG. 25H. The liner 712 may be used in conjunction with the longitudinal stripes 702, in one embodiment. The internal or external liner 712 may be a thin walled tube that has perforations 715 through the thickness of the liner that coaxially align with the plurality of the longitudinal stripes to facilitate expansion when a given radial force is applied, as shown in FIG. 25J. Alternatively, the integral liner 714 may include a plurality of elastic stripes 702 that do not penetrate the full wall thickness of the main sheath body 700, as shown in FIG. 25G. The liner may be constructed in a manner that allows more control over the amount of radial force that is required to expand the sheath 700. In one embodiment, the liner may be the controlling factor in expansion of the sheath, so the elastic portion could be constructed of materials as compliant as a balloon FIG. 25I. The force causing expansion could be a clot burdened filter or other mechanism built into the device (e.g.: an integral balloon or the temporary dilator, as previously described)

Figure 25K:
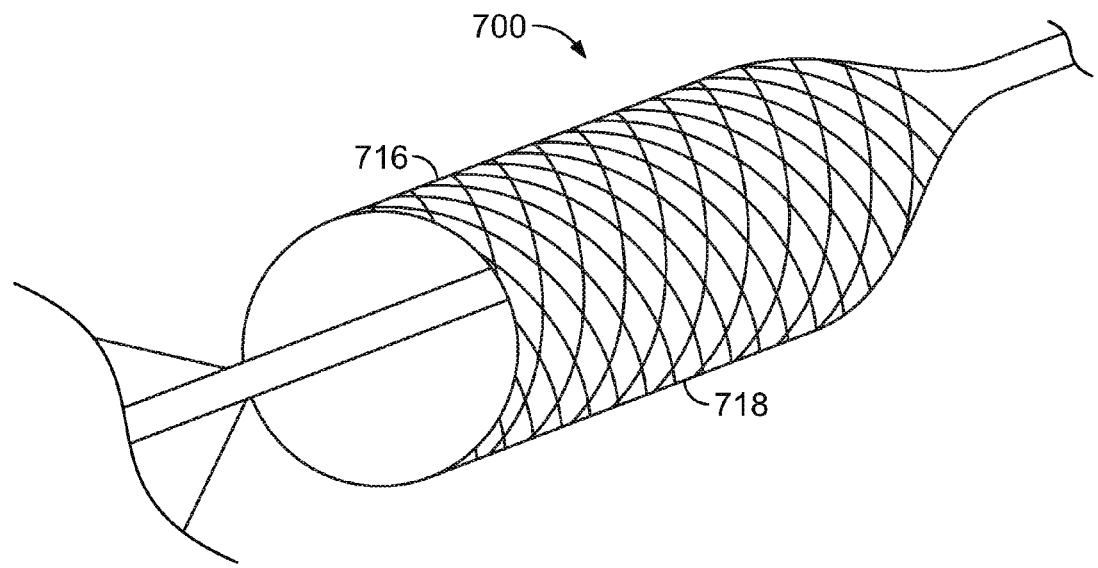
Figure 25L:
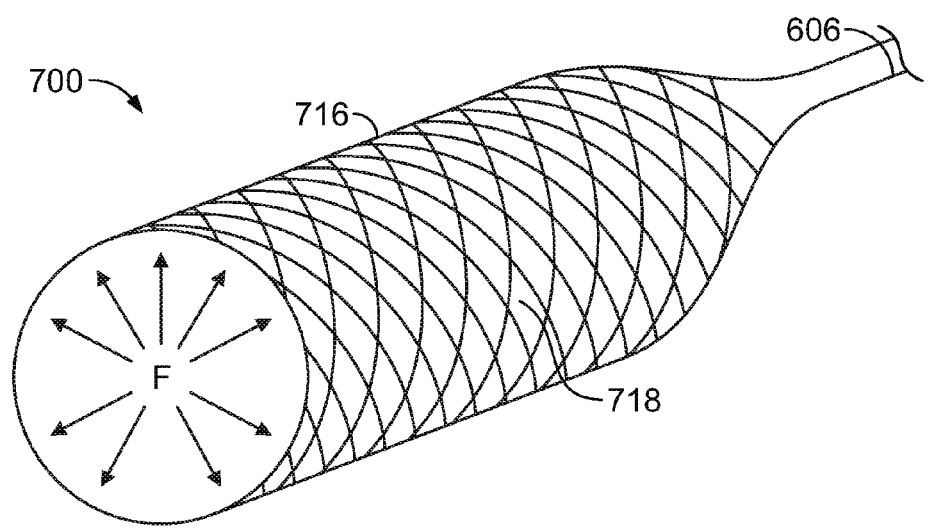
Figure 25M:
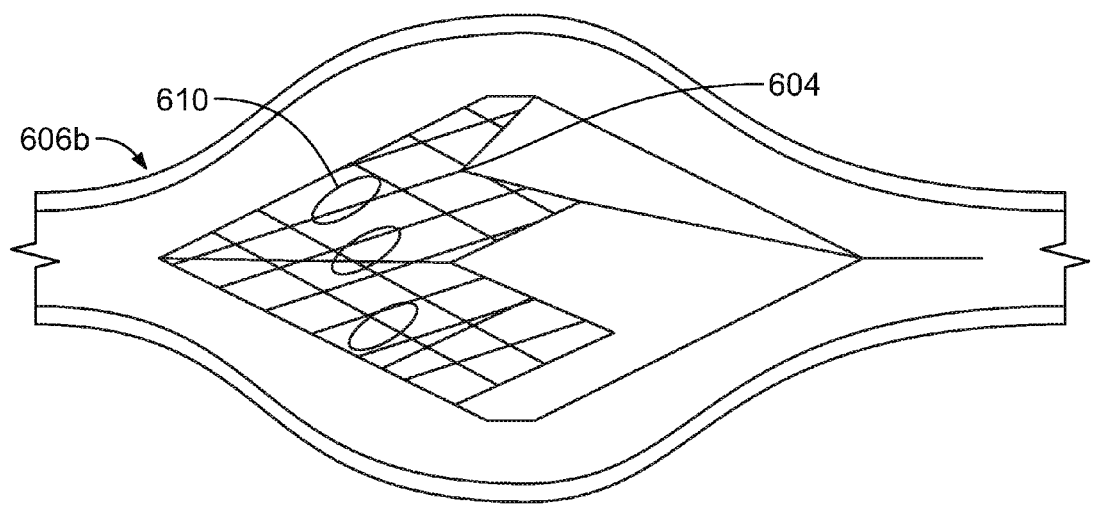

In an alternative embodiment, the expandable sheath may comprise a composite structure including an expandable frame 716 positioned on the distal end of the expandable sheath, as shown in FIGS. 25K-25L. In one embodiment, the expandable frame 716 includes a diamond pattern formed by a plurality of linear slits 718 in combination with an elastic matrix of the sheath tube 700. Alternative patterns may be formed by the plurality of linear slits such as polygonal, square, rectangular, triangular, circular, ellipsoidal, and the like. The frame 716 would serve as the control for the initial diameter (FIG. 25K) and the expanded diameter (FIG. 25L). The elastic matrix maintains a smooth surface on the inner and/or outer surfaces of the expandable tube 700 in the initial diameter state and the expanded diameter state. Depending of the material selection of the elastic matrix, the elastic matrix may be applied via an extrusion process, polymer reflow, dip coating, and the like. Control of the radial force F required to expand the tube would be controlled by the combination of the frame design and properties of the elastic matrix. A larger diamond pattern formed by the linear slits 718 may allow for a greater diameter expansion, while a smaller diamond pattern formed by the linear slits 718 may allow for a greater force and a smaller diameter expansion. The expandable frame 716 may also be coupled with liners 712 and 714, as described previously.

Figure 25N:
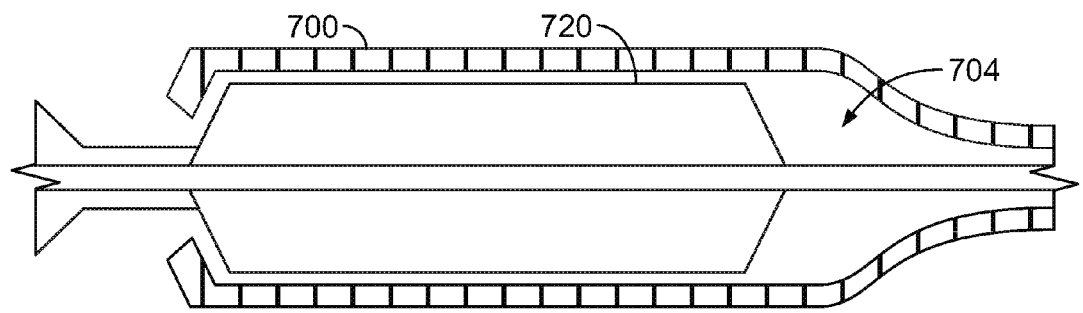

In one embodiment, the expandable sheath may be expanded by a balloon 720 prior to retrieval of the filter, as shown in FIG. 25N. The balloon 720 may be integral to the inner member within the lumen 704 of the expandable sheath and expanded to a larger diameter to activate the expandable sheath's elastic or expandable properties.

Basket or Guidewire to Capture Debris

Figure 26A:
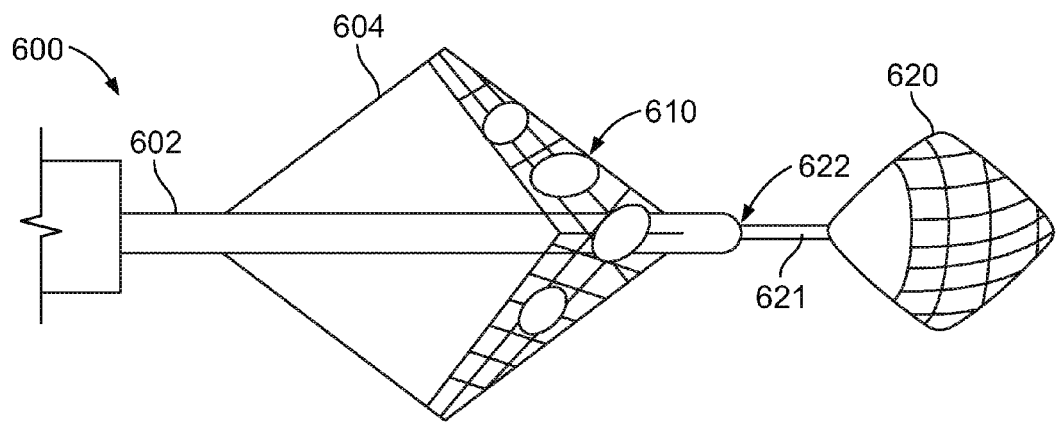
FIGS. 26A-26B are cross-sectional views of a basket introduced after clots are captured in the filter can be utilized to catch emboli that are released when the filter collapses.
Figure 26B:
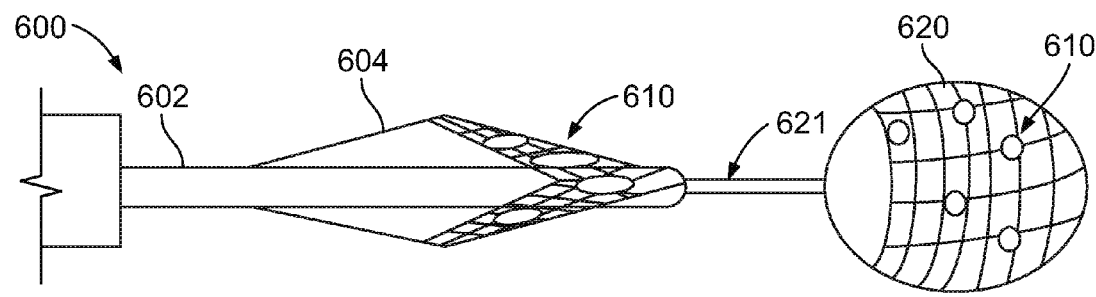

In one embodiment, a basket 620 is introduced into at least one lumen of the multi-lumen catheter body 600 after clots 610 are captured in the filter 604, whereby the basket 620 can be utilized to distally catch emboli 610 that are released when the filter 604 collapses to the contracted state, as shown in FIG. 26B. The basket 620 can be introduced through a lumen 622 of the multi-lumen catheter 600 or the basket 620 may be an accessory to the vena cava filter and catheter unit, as shown in FIG. 26A. The basket 620 expands to a larger diameter at least the diameter of the blood vessel, while the basket 620 captures the emboli released during filter collapse, such that the filter 604 can be removed, accordingly. In one embodiment, the basket 620 may be introduced when the filter 604 is being collapsed or removed. Unlike embolic filters that may be used for placement of stents, the basket 620 is intended to be used during retrieval of the filter and sized appropriately for the vena cava. The basket 620 may be included on a distal portion of a central shaft 621 to be incorporated with the vena cava filter 604. The basket 620 may be deployed by moving the central shaft 621 distally from the filter 604 during the removal of a device 600. Alternatively, the basket 620 may not be deployed when the emboli released from collapsing the filter 604 are physiologically irrelevant in such a way that the body can take care of the emboli with no harm to the patient.

Figure 26C:
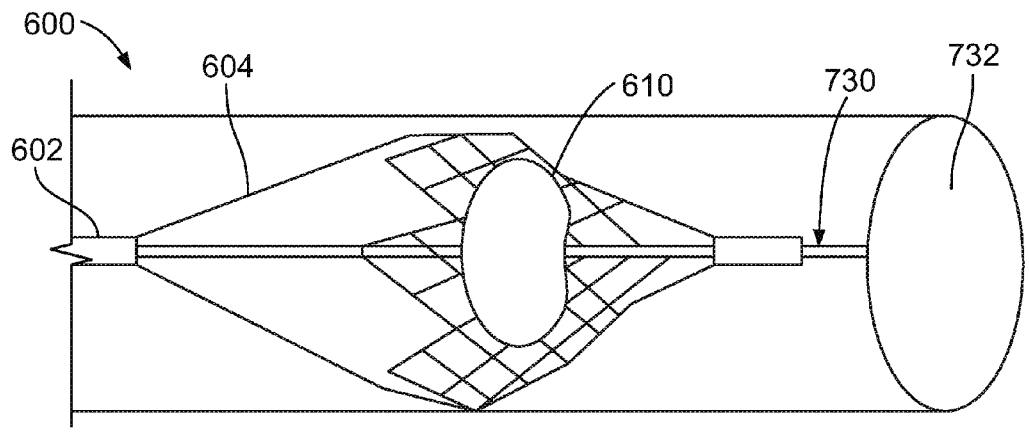
FIGS. 26C-26E are side views the guidewire with an occlusive member.
Figure 26D:
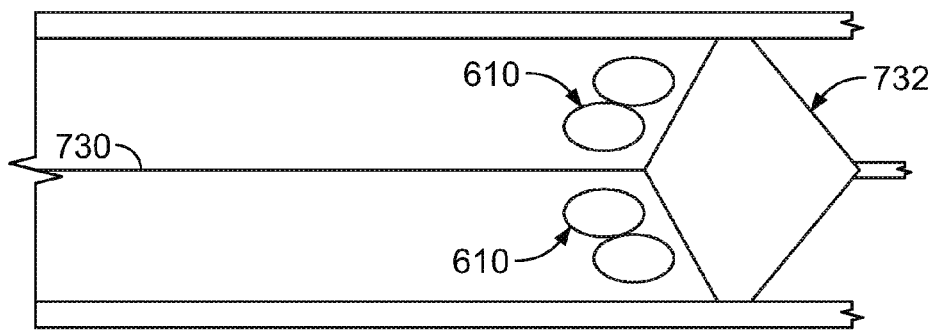
Figure 26E:
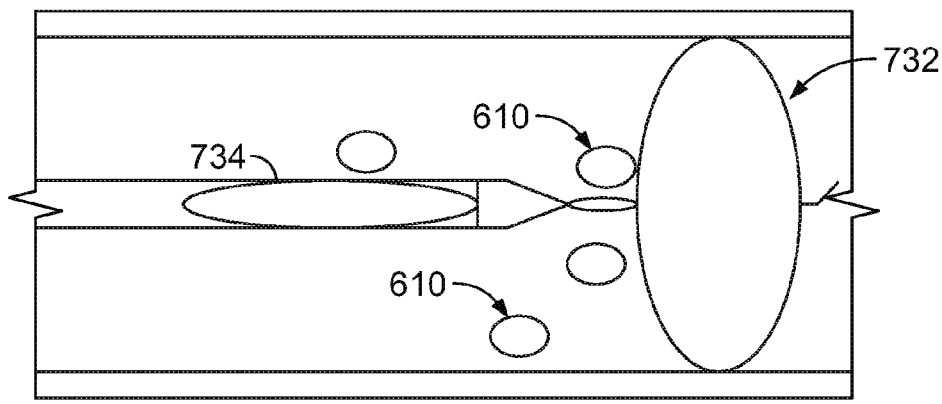

In one embodiment, a guidewire 730 is introduced through at least one lumen of the multi-lumen catheter body 600, and the guidewire 730 includes an occlusive member 732 on the distal end of the guidewire 730. The guidewire 730 may be coupled with the multi-lumen catheter 600 and be distally deployed from the filter in the expanded state when the filter 604 is clot 610 burdened. In one embodiment, the guidewire 730 is inserted through a lumen in the multi-lumen body 602 and the occlusive member 732 is located distal to the tip of the filter 604. The occlusive member 732 would be expanded to the vessel diameter to prevent embolic material 610 from traveling downstream or distal from the filter, as shown in FIG. 26C-26D. The multi-lumen catheter and filter could then be removed, leaving the guidewire 730 in place. A secondary device such as an aspiration catheter 734 could then be inserted over the guidewire 730 to evacuate any remaining clot 610 that is in the vessel, as shown in FIG. 26E. Alternatively, a lytic fluid may be introduced through the multi-lumen catheter to lyse the remaining clot 610 before the occlusive member 732 is retracted to its smaller diameter state and removed from the blood vessel.

In one embodiment, the guidewire 730 portion of the device could be constructed of a wire or tubular form that facilitates the expansion of the occlusive member 732. The occlusive member 732 could be a self-expanding structure (such as stent structure) or a balloon (compliant or rigid) that expands to the vessel diameter. To facilitate expansion of a balloon, it is possible to integrate a check valve in the device that permits the balloon to expand without losing volume when the syringe or other inflation device is disconnected. Additionally, the guidewire portion could be designed to be self-sealing when cut. The size or diameter of the occlusive member is to be in the range of femoral veins up to the vena cava. The diameter of the guidewire includes the ability to pass the guidewire through an existing lumen of multi-lumen catheter body. The aspiration catheter is able to pass over the guidewire through the same lumen, and depending on the guidewire, may require cutting off the proximal hub. And the occlusive member design facilitates aspiration of clot. The occlusive member could be a balloon or cage attached at the end of the wire. Alternatively, the distal end of the guidewire could be shaped such that it deploys in a manner similar to the birds nest filter or embolic coil, as described in commonly assigned U.S. patent application Ser. No. 13/031,037, herein incorporated by reference in its entirety. The guidewire could not include a proximal hub portion to facilitate the placement of the aspiration device through the multilumen catheter body. If guidewire has an integrated hub to facilitate expansion of the occlusive member, the guidewire could be designed in such manner to be temporary or removable.

Method for Clot Lysis

Figure 27A:
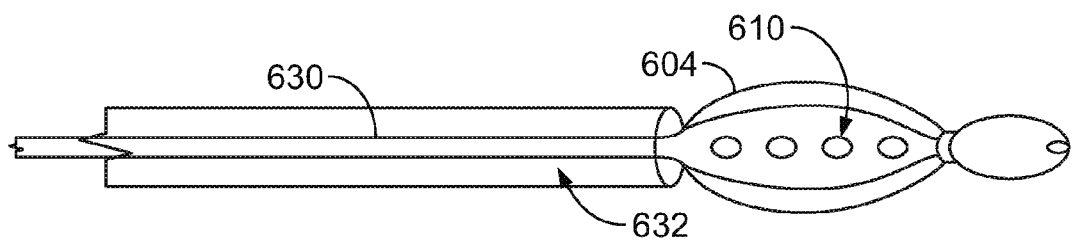
FIGS. 27A-27B are cross-sectional views of the vena cava filter has a lumen through which clot lysing medications could be delivered directly to the clot.
Figure 27B:
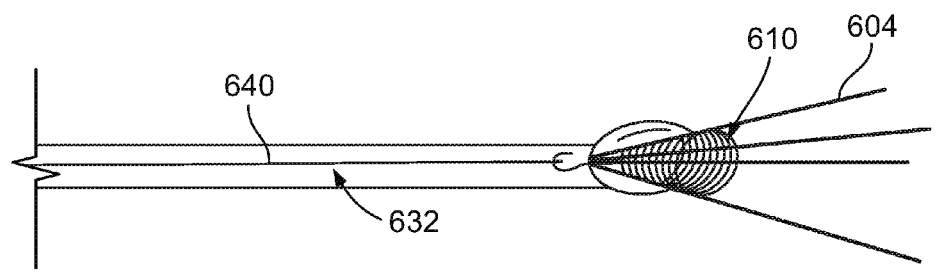

Vena cava filters disclosed herein are designed to capture/filter blood clots. These clots may dissolve over time or with the aid of medications, as described previously. Temporary vena cava filters 604 may have an integral retrieval system 630 associated with them or a separate retrieval system 640, as shown in FIGS. 27A-27B. In either case, the filter 604 being retrieved may have a clot 610 of random size morphology located at a random capture site in the filter 604. The retrieval/collapsing of the filter will cause the clot to be repositioned in a central coaxial location relative to the retrieval catheter/system. In one embodiment, the vena cava filter 604 has an annular lumen 632 through which clot lysing medications could be delivered directly to the clot 610, as shown in FIGS. 27A-27B. This relocates the clot to a position for potentially more effective lysing. Some methods typically leave the clot in position for lysing. However, the filter retrieval systems include or use a pre-existing lumen to direct clot lysing medications to thrombus in a partially retrieved filter.

Thrombolytic Scaffold

Figure 28:
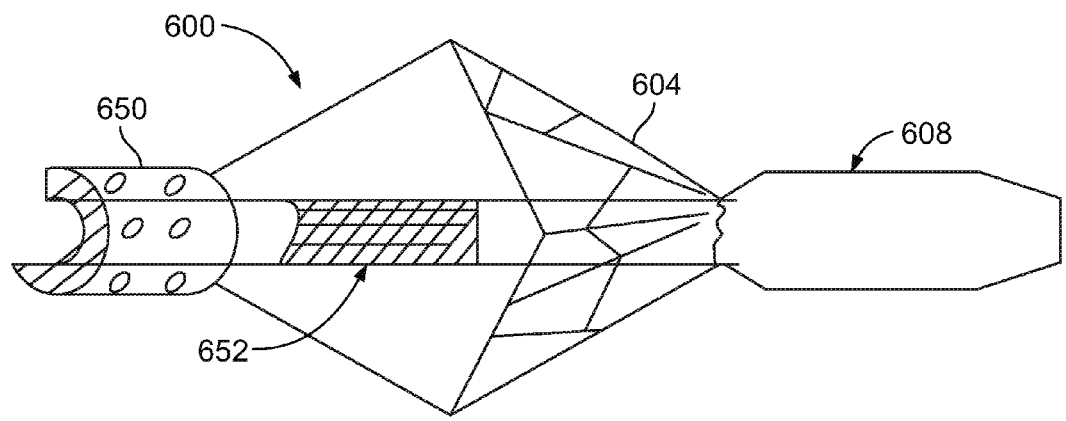
FIG. 28 is a cross-sectional view of a scaffold to elute thrombolytic drugs to prevent, minimize, or completely get rid of blood clots.

In one embodiment, a surface degradation scaffold 650 is attached or inherent in catheter body 600 that is positioned proximal to filter 604 or at clot location, as shown in FIG. 28. The scaffold 650 would elute thrombolytic drugs to prevent, minimize, or completely get rid of blood clots. The blood clot would be observed through fluoroscopic imaging and then a thrombolytic drug would be administered to destroy clot. This modification would not require observation as therapeutic agent would constantly prevent, minimize, or completely get rid of blood clot. Any thrombolytic agent could be utilized (tPa, Urokinase, Actiplase, and the like). An additional scaffold may be placed on the catheter body that is distal 652 from the first scaffold 650 for additional elution of thrombolytic drugs.

Any biocompatible surface degradation scaffold could be utilized. Vena Cava Filter could be attached to drug-eluting scaffold if permanent option is desirable. Normal drug elution rate could be controlled for maximum therapeutic delivery or minimized to allow use when anti-coagulants are contraindicated. The Scaffold could be near lumen flow pathway to allow bolus delivery if blood clot is observed (e.g. Temperature, Mechanical, Chemical means of increasing scaffold drug elution temporarily).

Mechanical Thrombolytic Filter

Figure 29A:
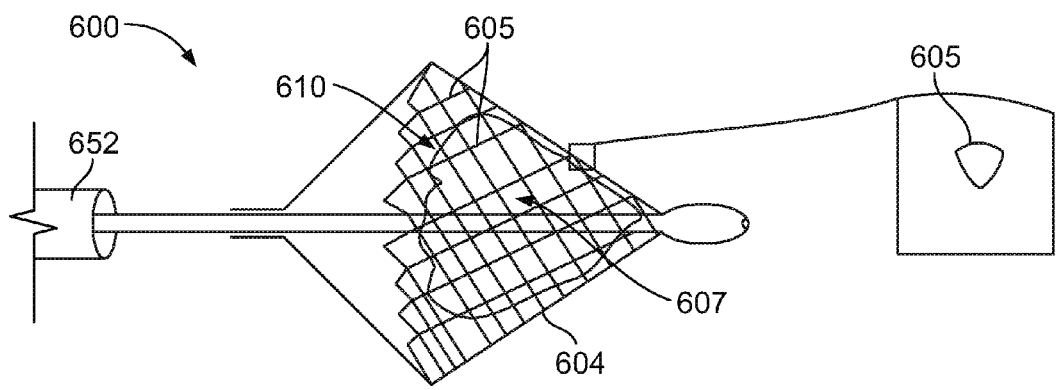
FIGS. 29A-29B are cross-sectional views of Vena Cava Filter is specifically designed to mechanically lyse blood clots.
Figure 29B:
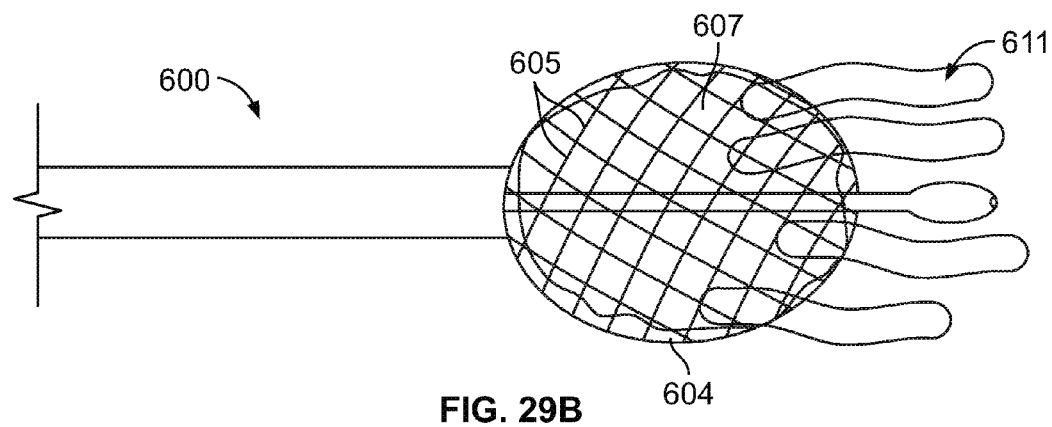

In one embodiment, the Vena Cava Filter 604 is specifically designed to mechanically lyse blood clots 610, as shown in FIG. 29A. With a blood clot within the expanded filter 604, the filter 604 would be retrieved and retracted thereby breaking the main blood clots 610 into smaller clots 611 that are clinically benign, as shown in FIG. 29B. The struts 605 would be shaped and orientated in such a way that maximizes the ability to shear through a blood clot during filter retrieval/collapse. The struts 605 would have an angled cross-section with a pointed tip directed at the central axis of the multi-catheter body. Alternatively, the struts 605 may act like scissors with adjacent struts as to provide a scissor action for any clot that is caught within the filter openings 607. The size of filter openings 607 between struts 605 would be small enough that as the blood clot 610 squeezes through the openings its size is reduced to clinically benign clots 611. This concept/modification optimizes the current vena cava filter design to mechanically lyse clots in addition to chemical lysis and the like, or as a single means for clot lysis.

Clot Detection Wires

Figure 30A:
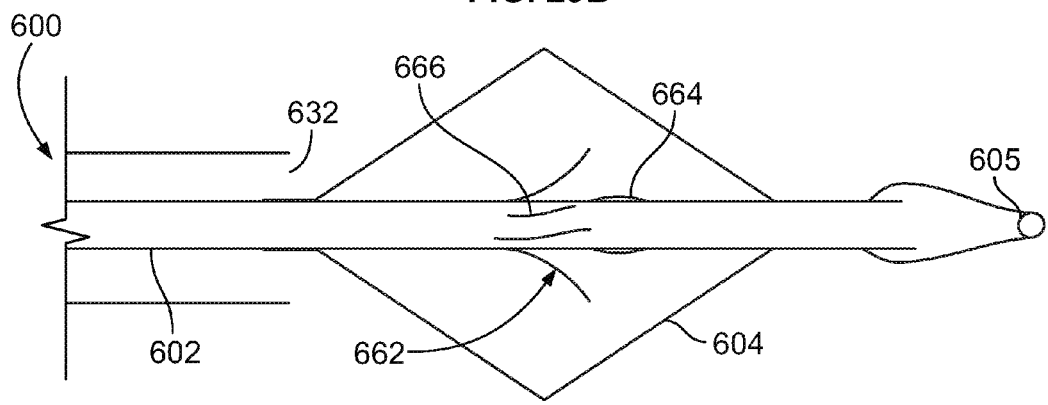
FIGS. 30A-30C are cross-sectional views of at least two wires along the length of the catheter to detect clots in the filter.
Figure 30B:
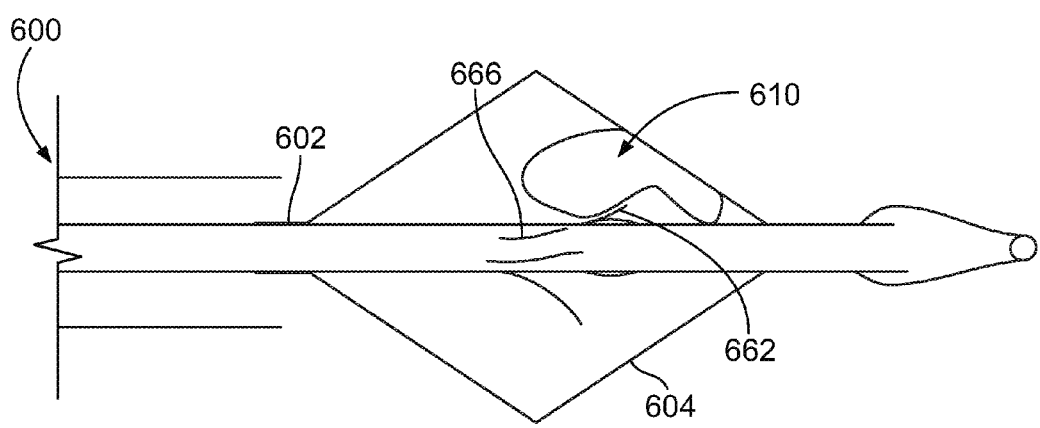
Figure 30C:
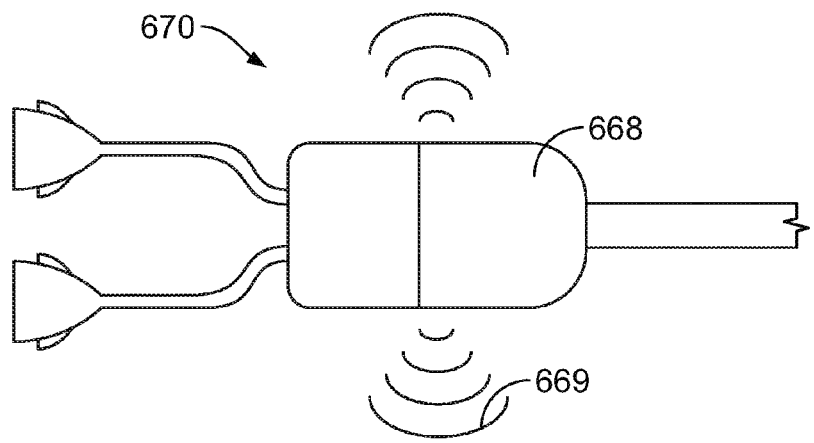

In one embodiment, at least two wires would run the longitudinal length of the catheter 600 from the proximal end of the catheter, as shown in FIGS. 30A-30C. On the hub side 670, the two wires are connected to an ohmmeter 668, as shown in FIG. 30C. On the filter 604 side, the first wire would be connected to an array of wires 662 disposed on the multi-lumen catheter body and within the filter 604 deployment, whereby the wires 662 point coaxially away from the central shaft or upward. Upon clot 610 presence, the wires 662 are pushed coaxially inward towards the central shaft 602, as shown in FIG. 30B. A second wire 666 would be connected to a cylindrical contact 664 bonded to the central shaft 602. A change in resistance could be detected upon the wires 662 in the array getting closer or making contact with the cylindrical contact 664. The change of resistance signal is sent through the wire 666 to indicate the presence of clot within the deployed filter. As shown in FIG. 30C, the ohmmeter 668 could be internal or external to the device. Upon change in resistance (indicative of clot presence) multiple methods of an alert 669 could be utilized, such as an audible alert, visual alert, electrical alert, and the like. Many different configurations/geometries of wires, cylinders, plates, etc. could be utilized on the filter side. Any method of detection in wire movement could be utilized in place of the ohmmeter.

Figure 30D:
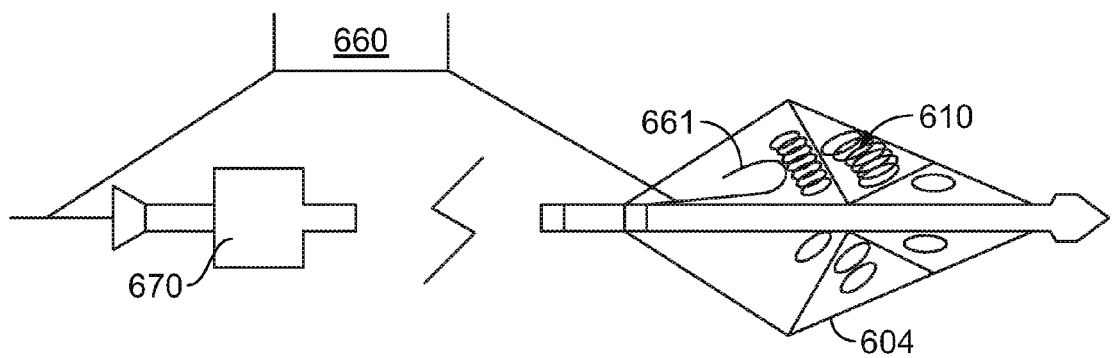
FIGS. 30D-30J are side views of alternative embodiments of the clot detection wires.

In another embodiment, the clot detection wire 660 includes a distal looped configuration 661, as shown in FIG. 30D. The distal looped configuration 661 is used to detect when a clot 610 is captured in the filter 604, and the clot detection wire 660 is inserted through a proximal port on the hub, which leads directly to the deployed filter basket. The distal looped configuration 661 provides tactile sensation when a clot 610 is present due to the increase resistance. Also, the wire can be shape-set to a particular conformation, and deformation of its shape, indicates that there is a clot in the filter basket. An X-Ray image may be taken to identify the deformation of the wire with respect to the filter. The device will allow for the multi-lumen catheter to be removed bedside in patients with no or minimal blood clots trapped in the filter. The procedure will reduce the number of unnecessary cavograms.

Figure 30E:
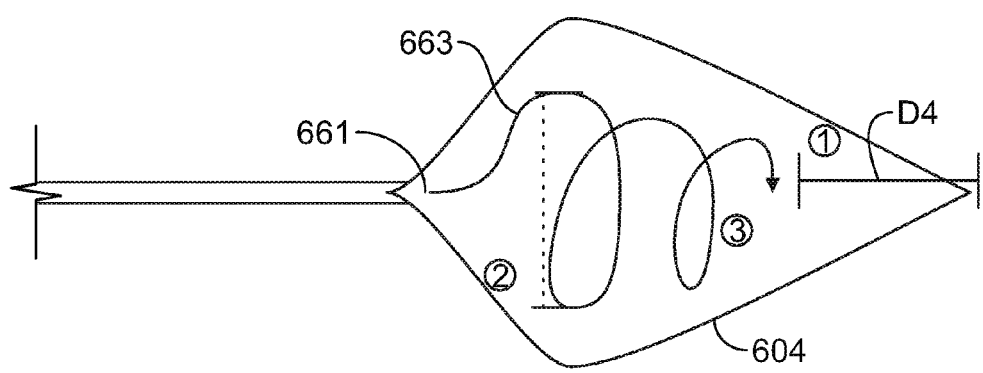
Figure 30F:
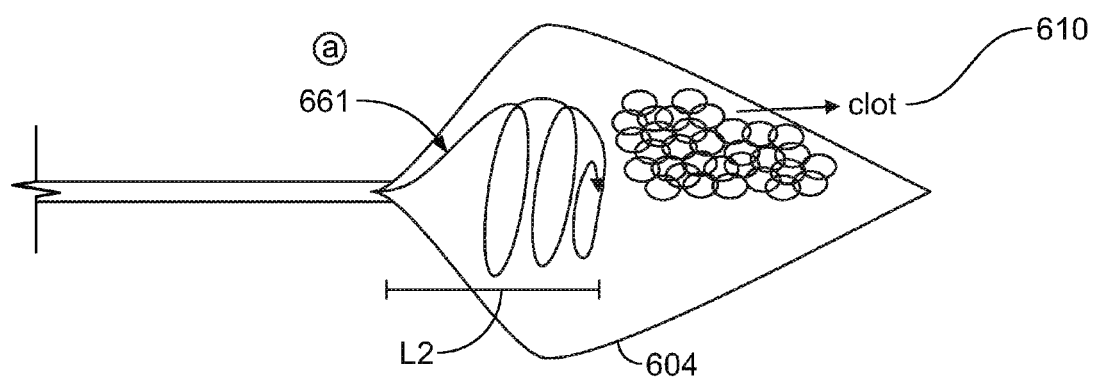
Figure 30G:
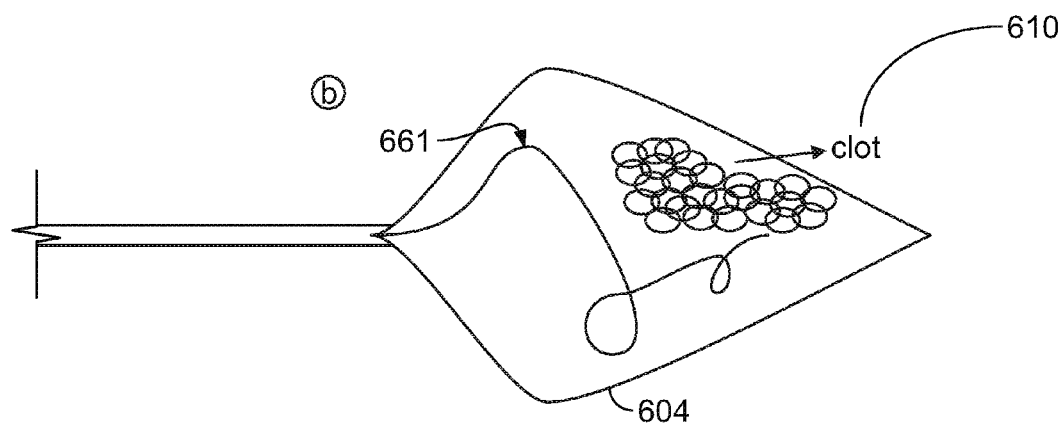

In one embodiment, the distal looped configuration 661 ends at a distance D4 from the distal end of the filter 604, as shown in FIG. 30E. As the wire 660 is distally advanced through the expanded filter configuration, the distal end of the wire 600 may form the looped configuration 661 including a plurality of loops, whereby the diameter of the largest loop 663 is within the expandable range of the filter. In one embodiment, the total length of the distal loop configuration 661 is captured within the region defined by the expanded filter geometry. The loop area includes a minimal radial force to allow the expansion of the full looped configuration. The wire 660 may include a positive stop with luer when the distal looped configuration has been formed and the clot is detected, or the wire can have depth indicators where a certain length of the wire 660 is looped in the distal end and the clot is detected, as shown in FIG. 30F. The length L2 of the distal looped configuration 661 is less than the original defined length or the distance D4 is increased from the distal end of the filter, then clot 610 presence is detected. However, if the distal looped configuration is poorly formed, as shown in FIG. 30G, then the clot detection wire 660 may be proximally removed for another attempt at clot detection. If the final length of the loop is very short such that the looped configuration does not fully expand or achieve the entire looped configuration length, it may indicate a presence of large clots 610. Clot detection may be tactile or confirmed via standard X-ray. Tactile detection may be if the looped configuration does not fully expand, then resistance for the wire may be sensed on the proximal hub. The proximal hub may be employed as described in commonly assigned U.S. patent application Ser. No. 13/737,694, herein incorporated by reference in its entirety. The wire may include or be constructed of radiopaque material to enhance visualization during X-ray assessment. The visual interpretation of the clot detection test is whether a poorly formed or non-formed loop, or a compressed (short loop) indicates the need to evaluate the filter before removal with a cavogram.

Figure 30H:
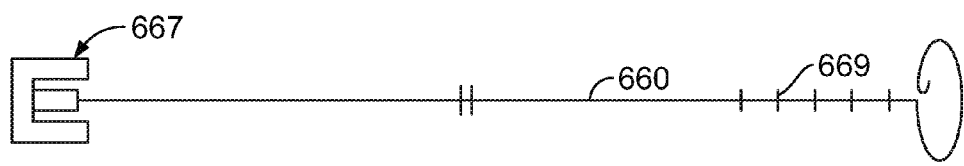
Figure 30I:
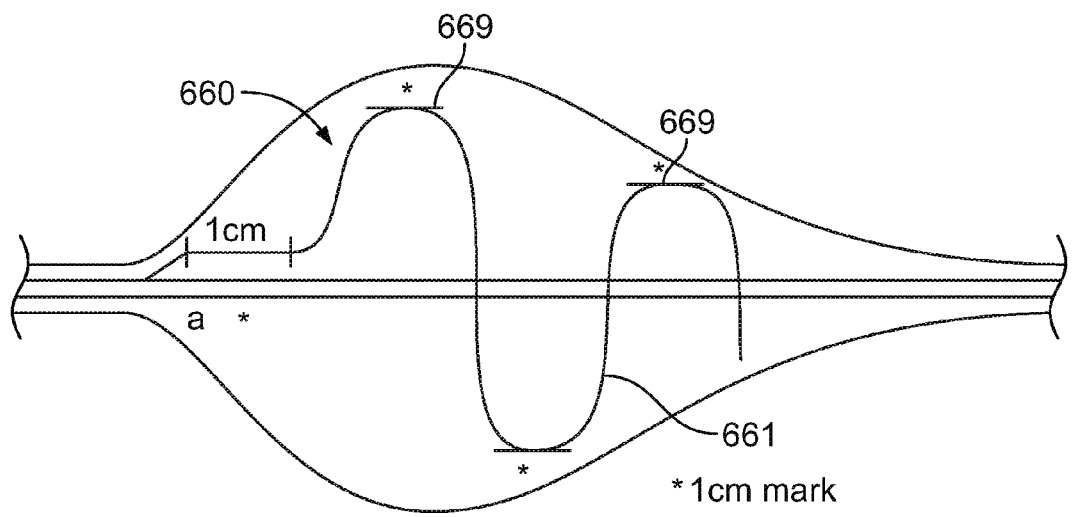
Figure 30J:
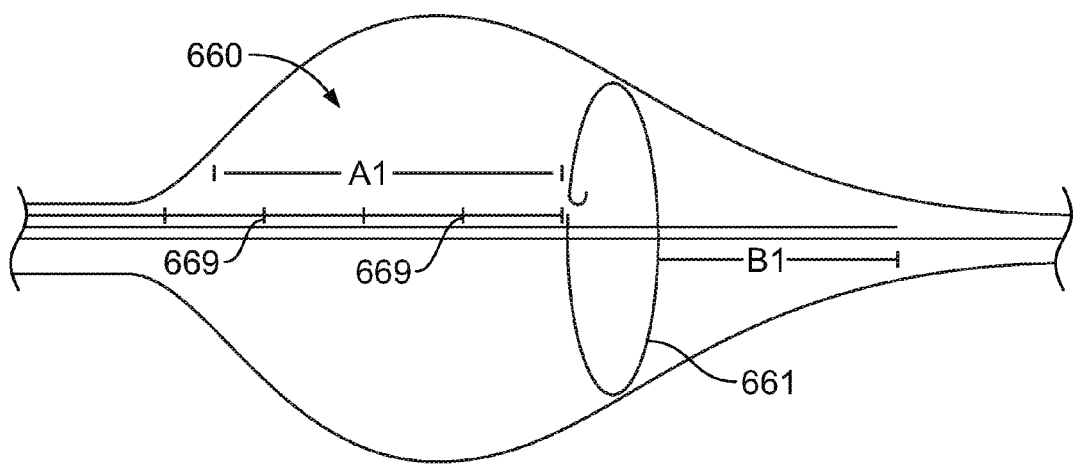

The clot detection wire 660 can be placed within the multi-lumen catheter body, where the proximal end of the wire at the hub includes a luer 667 connector, as shown in FIG. 30H. The luer connector or depth markers 669 on the wire ensure that the wire is not inserted beyond its intended insertion depth or beyond the distal tip of the filter. The wire 660 can be made from different materials: stainless steel (different grades), Nitinol, coni-chrome, polymer, shape memory polymer, etc. The wire's distal end can be shape set or just have the shape of various configurations: coil, cone, sinusoidal, no defined shape, and the like. The wire can be inserted through various access port (not just Medial Filter Port): contralateral, caudal, cranial, etc. The dimension of the wire can be modified to provide the appropriate mechanical properties. It does not have to be a wire; it can also be a tube or rod. The device can be used with other vena cava filters. The wire can be design as a strain gauge in which a strain or resistance value indicates a thrombus in the filter. The wire can include a mark or tab 669 at defined distances along the distal end of the wire 660, as shown in FIGS. 30I and 30J. In one embodiment wire 660 includes a generally sinusoidal configuration 661 with marks 669 at defined distances along the distal end, such that if the wire 660 is not expanded in the sinusoidal configuration 661, then the marks 669 are collapsed as an indication of an obstruction or a clot in the filter, as shown in FIG. 30I. In one embodiment, the distal looped configuration 661 includes a single looped wire configuration, as shown in FIG. 30J, where the single loop moves to set distance B1 from the distal end filter and distance of A1 from the proximal end of the filter. And if the loop is not at a distance B1 from the distal end of the filter and a distance A1 from the proximal end of the filter, or if the loop is poorly formed or not perpendicular to the multi-lumen catheter body, there is an obstruction in the filter or clot presence detected.

Device Removal Technique for Large Clots

Figure 31A:
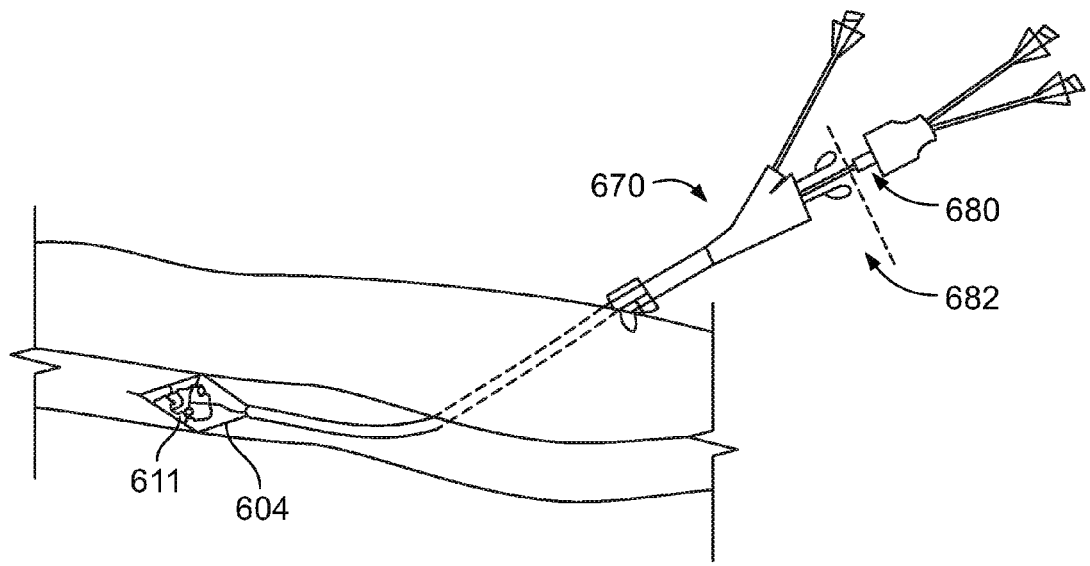
FIGS. 31A-31C is a cross-sectional view of the removal of the device in cases where a large clot burden is present in the filter basket.
Figure 31B:
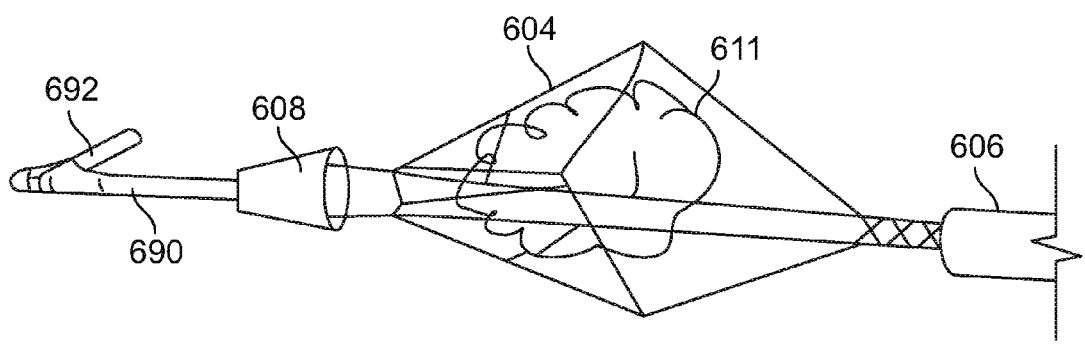
Figure 31C:
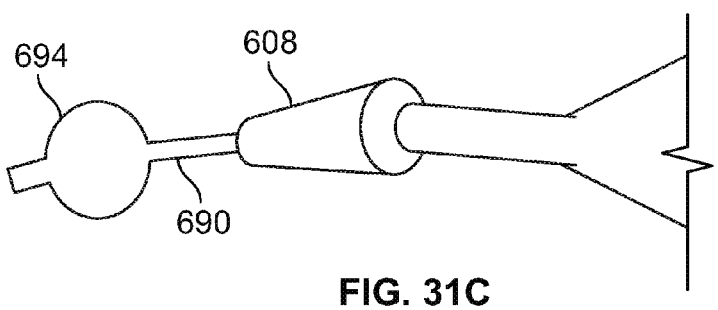

In one embodiment, as shown in FIGS. 31A-31C, the removal of the device in cases where a large clot burden 611 is present in the filter 604 includes the following: partially retrieving the multi-lumen catheter hub 680, cutting 682 the multi-lumen catheter body at the proximal end; inserting a balloon or a guide-wire 690 with a Barb 692 through distal lumen tip 608, as shown in FIG. 31B. A secondary device may be used to secure the multi-lumen catheter body in place prior to insertion of balloon/wire 690. Additional steps include inflating the balloon 694 past catheter tip FIG. 31C (or engage barb 692 FIG. 31B); and removing the Outer sheath 606. After the sheath is removed, a larger introducer sheath and dilator could be inserted over the wire and multi-lumen catheter body. Once in place, the dilator would be removed, and the clot burdened filter could be retrieved into the larger introducer sheath. This procedure has the advantage of allowing for full containment of the filter with a large clot burden. This could allow for the removal of the clot instead of breaking it into small pieces which would need to be dealt with in other manners.

These and other aspects of the present invention are provided by way of non-limiting examples, with the claims appended hereto serving to define the scope of the subject matter regarded as the invention.

What is claimed is:

1. A medical device, comprising:
  a. a multi-lumen catheter body having a first open port associated with a first fluid flow lumen and a second open port associated with a second fluid flow lumen;
  b. a filter member having a first end immovably coupled to the multi-lumen catheter body and a second end movable relative to the multi-lumen catheter body, the filter member being positioned substantially intermediate the first open port and the second open port such that the first open port is proximal the filter member and the second open port is distal the filter member, the filter member having a diametrically enlarged central opening which opens toward a patient's blood flow, at least one infusion port associated with at least one infusion lumen in the multi-lumen catheter body and positioned within an area of the multi-lumen catheter body bounded by the filter member;
  c. a clot management device operably coupled with the filter member, comprising a clot detection wire disposed within at least one lumen of the multi-lumen catheter body, wherein the clot detection wire includes a distal looped configuration when disposed within the filter member in an expanded state; and
  d. the clot detection wire includes a plurality of depth markers at defined distances along a distal end of the clot detection wire, wherein if the distal looped configuration is not expanded within the expanded state of the filter member, then the plurality of depth markers are collapsed to indicate a clot within the filter member.

2. The medical device according to claim 1, wherein the distal looped configuration deforms its shape during the presence of a clot in the filter member.

3. The medical device according to claim 1, wherein the distal looped configuration ends at a distance from a distal end of the filter to form a plurality of loops, whereby the plurality of loops may be displaced by the clot within the filter member and increase the distance to detect the clot.

4. The medical device according to claim 3, wherein the clot detection wire includes radiopaque material.

5. The medical device system of claim 1 further comprising an introducer sheath operably coupled over the multi-lumen catheter body, wherein the filter member burdened with a clot is retrieved into the introducer sheath.

6. A medical device system for detecting clots in a vena cava filter, comprising:
  a. a multi-lumen catheter body having a first open port associated with a first fluid flow lumen and a second open port associated with a second fluid flow lumen;
  b. a filter member having a first end immovably coupled to the multi-lumen catheter body and a second end movable relative to the multi-lumen catheter body, the filter member being positioned substantially intermediate the first open port and the second open port such that the first open port is proximal the filter member and the second open port is distal the filter member, the filter member having a diametrically enlarged central opening which opens toward a patient's blood flow, at least one infusion port associated with at least one infusion lumen in the multi-lumen catheter body and positioned within an area of the multi-lumen catheter body bounded by the filter member;
  c. at least a first clot detection wire and a second clot detection wire, each of the at least first clot detection wire and second clot detection wire capable of being passed through a lumen of the multi-lumen catheter body and extending from a proximal end to a distal end of the multi-lumen catheter body and extending into the central opening of the filter member;
  d. the first clot detection wire and the a second clot detection wire are operably connected to an ohmmeter on a hub side of the multi-lumen catheter body; and
  e. the first clot detection wire points coaxially away from a central shaft of the filter member and the second clot detection wire is operably positioned on the central shaft and near the first clot detection wire.

7. The medical device according to claim 6, wherein the first clot detection wire contacts the second clot detection wire to provide a change of resistance signal detecting the clot.

8. The medical device system of claim 6 further comprising an introducer sheath operably coupled over the multi-lumen catheter body, wherein the filter member burdened with a clot is retrieved into the introducer sheath.

* * * * *